(12) United States Patent
Wu

(10) Patent No.: US 9,051,329 B2
(45) Date of Patent: Jun. 9, 2015

(54) TRICYCLIC HETEROCYCLES USEFUL AS DIPEPTIDYL PEPTIDASE-IV INHIBITORS

(75) Inventor: Wen-Lian Wu, Edison, NJ (US)

(73) Assignee: Merck Sharp & Dohme Corp., Rahway, NJ (US)

(*) Notice: Subject to any disclaimer, the term of this patent is extended or adjusted under 35 U.S.C. 154(b) by 0 days.

(21) Appl. No.: 14/125,116

(22) PCT Filed: Jul. 2, 2012

(86) PCT No.: PCT/US2012/045182
§ 371 (c)(1),
(2), (4) Date: Dec. 10, 2013

(87) PCT Pub. No.: WO2013/006526
PCT Pub. Date: Jan. 10, 2013

(65) Prior Publication Data
US 2014/0113920 A1   Apr. 24, 2014

Related U.S. Application Data

(60) Provisional application No. 61/504,559, filed on Jul. 5, 2011.

(51) Int. Cl.
*A61K 31/505* (2006.01)
*C07D 491/00* (2006.01)
*C07D 487/14* (2006.01)
*A61K 31/519* (2006.01)
*A61K 31/529* (2006.01)

(52) U.S. Cl.
CPC ............ *C07D 487/14* (2013.01); *A61K 31/519* (2013.01); *A61K 31/529* (2013.01)

(58) Field of Classification Search
None
See application file for complete search history.

(56) References Cited

U.S. PATENT DOCUMENTS

| | | | |
|---|---|---|---|
| 5,939,560 | A | 8/1999 | Jenkins et al. |
| 6,166,063 | A | 12/2000 | Villhauer |
| 6,303,661 | B1 | 10/2001 | Demuth et al. |
| 6,699,871 | B2 | 3/2004 | Edmondson et al. |
| 6,890,898 | B2 | 5/2005 | Bachovchin et al. |
| 7,078,381 | B2 | 7/2006 | Bachovchin et al. |
| 7,407,955 | B2 | 8/2008 | Himmelsbach et al. |
| 7,459,428 | B2 | 12/2008 | Bachovchin et al. |
| 8,119,648 | B2 | 2/2012 | Himmelsbach et al. |
| 8,178,541 | B2 | 5/2012 | Himmelsbach et al. |
| 2009/0018331 | A1 | 1/2009 | Yoshikawa et al. |

FOREIGN PATENT DOCUMENTS

| | | | |
|---|---|---|---|
| DE | 10109021 A1 * | 9/2002 | |
| WO | WO9740832 | 11/1997 | |
| WO | WO9819998 | 5/1998 | |
| WO | WO02076450 A1 | 10/2002 | |
| WO | WO03000180 A2 | 1/2003 | |
| WO | WO03000181 A2 | 1/2003 | |
| WO | WO 03004496 A1 * | 1/2003 | |
| WO | WO03004498 A1 | 1/2003 | |
| WO | WO03082817 A2 | 10/2003 | |
| WO | WO2004007468 A1 | 1/2004 | |
| WO | WO2004018469 A1 | 3/2004 | |
| WO | WO2004032836 A2 | 4/2004 | |
| WO | WO2004037169 A2 | 5/2004 | |
| WO | WO2004043940 A1 | 5/2004 | |
| WO | WO2004050022 A2 | 6/2004 | |
| WO | WO2004058266 A1 | 7/2004 | |
| WO | WO2004064778 A2 | 8/2004 | |
| WO | WO2004069162 A2 | 8/2004 | |
| WO | WO2004096806 A1 | 11/2004 | |
| WO | WO2004103276 A2 | 12/2004 | |
| WO | WO2004110436 A1 | 12/2004 | |
| WO | WO2004112701 A2 | 12/2004 | |
| WO | WO2005011581 A2 | 2/2005 | |
| WO | WO2005044195 A2 | 5/2005 | |
| WO | WO2005108382 A1 | 11/2005 | |
| WO | WO2005116029 A1 | 12/2005 | |
| WO | WO2006009886 A1 | 1/2006 | |
| WO | WO2006023750 A2 | 3/2006 | |
| WO | WO2006039325 A2 | 4/2006 | |
| WO | WO2006058064 | 6/2006 | |
| WO | WO2006065826 A2 | 6/2006 | |
| WO | WO2006078676 A2 | 7/2006 | |
| WO | WO2006104997 A2 | 10/2006 | |
| WO | WO2006119260 A2 | 11/2006 | |
| WO | WO2006127530 A2 | 11/2006 | |
| WO | WO2007024993 A2 | 3/2007 | |
| WO | WO2007035198 A2 | 3/2007 | |
| WO | WO2007070434 A2 | 6/2007 | |
| WO | WO2007078726 A2 | 7/2007 | |
| WO | WO2007087231 A2 | 8/2007 | |
| WO | WO2007097931 A2 | 8/2007 | |
| WO | WO2007126745 A2 | 11/2007 | |
| WO | WO2007136603 A2 | 11/2007 | |
| WO | WO2008060488 A1 | 5/2008 | |
| WO | WO2009025784 A1 | 2/2009 | |
| WO | WO2010056708 A1 | 5/2010 | |
| WO | WO2011028455 A1 | 3/2011 | |
| WO | WO2011146358 A1 | 11/2011 | |
| WO | WO2012078448 | 6/2012 | |
| WO | WO2012118945 | 9/2012 | |

* cited by examiner

*Primary Examiner* — Jeffrey S Lundgren
*Assistant Examiner* — Michael Schmitt
(74) *Attorney, Agent, or Firm* — Janet E. Fair; Catherine D. Fitch

(57) ABSTRACT

The present invention is directed to novel tricyclic heterocycles of structural formula (I) which are inhibitors of the dipeptidyl peptidase-IV enzyme and which are useful in the treatment or prevention of diseases in which the dipeptidyl peptidase-IV enzyme is involved, such as diabetes and particularly Type 2 diabetes. The invention is also directed to pharmaceutical compositions comprising these compounds and the use of these compounds and compositions in the prevention or treatment of such diseases in which the dipeptidyl peptidase-IV enzyme is involved.

(I)

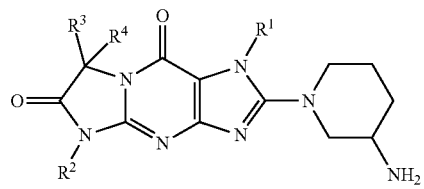

18 Claims, No Drawings

TRICYCLIC HETEROCYCLES USEFUL AS DIPEPTIDYL PEPTIDASE-IV INHIBITORS

CROSS REFERENCE TO RELATED APPLICATIONS

This application is the National Stage of International Application No. PCT/US2012/045182, filed 02 Jul. 2012, which claims the benefit under 35 U.S.C. 119(e) of U.S. Provisional Application No. 61/504,559, filed 5 Jul. 2011.

FIELD OF THE INVENTION

The present invention relates to tricyclic heterocycles which are inhibitors of the dipeptidyl peptidase-IV enzyme ("DPP-4 inhibitors") and which are useful in the treatment of diseases in which the dipeptidyl peptidase-IV enzyme is involved, such as diabetes and particularly Type 2 diabetes. The invention is also directed to pharmaceutical compositions comprising these compounds and the use of these compounds and compositions in the treatment of such diseases in which the dipeptidyl peptidase-IV enzyme is involved.

BACKGROUND

Diabetes refers to a disease process derived from multiple causative factors and characterized by elevated levels of plasma glucose or hyperglycemia in the fasting state or after administration of glucose during an oral glucose tolerance test. Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type 2 diabetes mellitus are at especially increased risk of macrovascular and microvascular complications, including coronary heart disease, stroke, peripheral vascular disease, hypertension, nephropathy, neuropathy, and retinopathy. Therefore, therapeutical control of glucose homeostasis, lipid metabolism and hypertension are critically important in the clinical management and treatment of diabetes mellitus.

There are two generally recognized forms of diabetes. In Type 1 diabetes, or insulin-dependent diabetes mellitus (IDDM), patients produce little or no insulin, the hormone which regulates glucose utilization. In Type 2 diabetes, or noninsulin dependent diabetes mellitus (NIDDM), patients often have plasma insulin levels that are the same or even elevated compared to nondiabetic subjects; however, these patients have developed a resistance to the insulin stimulating effect on glucose and lipid metabolism in the main insulin-sensitive tissues, which are muscle, liver and adipose tissues, and the plasma insulin levels, while elevated, are insufficient to overcome the pronounced insulin resistance.

Insulin resistance is not primarily due to a diminished number of insulin receptors but to a post-insulin receptor binding defect that is not yet understood. This resistance to insulin responsiveness results in insufficient insulin activation of glucose uptake, oxidation and storage in muscle and inadequate insulin repression of lipolysis in adipose tissue and of glucose production and secretion in the liver.

The available treatments for Type 2 diabetes, which have not changed substantially in many years, have recognized limitations. While physical exercise and reductions in dietary intake of calories will dramatically improve the diabetic condition, compliance with this treatment is very poor because of well-entrenched sedentary lifestyles and excess food consumption, especially of foods containing high amounts of saturated fat. Increasing the plasma level of insulin by administration of sulfonylureas (e.g. tolbutamide and glipizide) or meglitinide, which stimulate the pancreatic β cells to secrete more insulin, and/or by injection of insulin when sulfonylureas or meglitinide become ineffective, can result in insulin concentrations high enough to stimulate the very insulin-resistant tissues. However, dangerously low levels of plasma glucose can result from administration of insulin or insulin secretagogues (sulfonylureas or meglitinide), and an increased level of insulin resistance due to the even higher plasma insulin levels can occur. The biguanides increase insulin sensitivity resulting in some correction of hyperglycemia. However, the two biguanides, phenformin and metformin, can induce lactic acidosis and nausea/diarrhea. Metformin has fewer side effects than phenformin and is often prescribed for the treatment of Type 2 diabetes.

The glitazones (i.e. 5-benzylthiazolidine-2,4-diones) constitute an additional class of compounds with potential for ameliorating many symptoms of Type 2 diabetes. These agents substantially increase insulin sensitivity in muscle, liver and adipose tissue in several animal models of Type 2 diabetes resulting in partial or complete correction of the elevated plasma levels of glucose without occurrence of hypoglycemia. The glitazones that are currently marketed are agonists of the peroxisome proliferator activated receptor (PPAR), primarily the PPAR-gamma subtype. PPAR-gamma agonism is generally believed to be responsible for the improved insulin sensitization that is observed with the glitazones. Newer PPAR agonists that are being tested for treatment of Type 2 diabetes are agonists of the alpha, gamma or delta subtype, or a combination of these, and in many cases are chemically different from the glitazones (i.e., they are not thiazolidinediones in structure). Serious side effects (e.g. liver toxicity) have occurred with some of the glitazones, such as troglitazone.

Additional methods of treating the disease are still under investigation. New biochemical approaches that have been recently introduced or are still under development include alpha-glucosidase inhibitors (e.g. acarbose), GLP-1 mimetics (e.g., exenatide and liraglutide), glucagon receptor antagonists, glucokinase activators, and GPR-119 agonists.

Compounds that are inhibitors of the dipeptidyl peptidase-IV ("DPP-4") enzyme have also been found useful for the treatment of diabetes, particularly Type 2 diabetes [See WO 97/40832; WO 98/19998; U.S. Pat. Nos. 5,939,560; 6,303,661; 6,699,871; and 6,166,063; *Bioorg. Med. Chem. Lett.*, 6: 1163-1166 (1996); *Bioorg. Med. Chem. Lett.*, 6: 2745-2748 (1996); D. J. Drucker in *Exp. Opin. Invest. Drugs*, 12: 87-100 (2003); K. Augustyns, et al., *Exp. Opin. Ther. Patents*, 13: 499-510 (2003); Ann E. Weber, *J. Med. Chem.*, 47: 4135-4141 (2004); J. J. Holst, *Exp. Opin. Emerg. Drugs*, 9: 155-166 (2004); D. Kim, et al., *J. Med. Chem.*, 48: 141-151 (2005); K. Augustyns, *Exp. Opin. Ther. Patents*, 15: 1387-1407 (2005); H.-U. Demuth in *Biochim. Biophys. Acta*, 1751: 33-44 (2005); and R. Mentlein, *Exp. Opin. Invest. Drugs*, 14: 57-64 (2005).

Additional patent publications that disclose DPP-4 inhibitors useful for the treatment of diabetes are the following: WO 2006/009886 (26 Jan. 2006); WO 2006/039325 (13 Apr. 2006); WO 2006/058064 (1 Jun. 2006); WO 2006/127530 (30 Nov. 2006); WO 2007/024993 (1 Mar. 2007); WO 2007/070434 (21 Jun. 2007); WO 2007/087231 (2 Aug. 2007); WO 07/097,931 (30 Aug. 2007); WO 07/126,745 (8 Nov. 2007); WO 07/136,603 (29 Nov. 2007); and WO 08/060,488 (22 May 2008). The usefulness of DPP-4 inhibitors in the treatment of Type 2 diabetes is based on the fact that DPP-4 in vivo readily inactivates glucagon like peptide-1 (GLP-1) and gastric inhibitory peptide (GIP). GLP-1 and GIP are incretins and are produced when food is consumed. The incretins stimulate production of insulin. Inhibition of DPP-4 leads to decreased inactivation of the incretins, and this in turn results in increased effectiveness of the incretins in stimulating production of insulin by the pancreas. DPP-4 inhibition therefore results in an increased level of serum insulin. Advantageously, since the incretins are produced by the body only when food is consumed, DPP-4 inhibition is not expected to increase the level of insulin at inappropriate times, such as between meals, which can lead to excessively low blood sugar (hypoglycemia). Inhibition of DPP-4 is therefore expected to increase insulin without increasing the risk of hypoglycemia, which is a dangerous side effect associated with the use of insulin secretagogues.

DPP-4 inhibitors also have other therapeutic utilities, as discussed herein. New compounds are needed so that improved DPP-4 inhibitors can be found for the treatment of diabetes and potentially other diseases and conditions. In particular, there is a need for DPP-4 inhibitors that are selective over other members of the family of serine peptidases that includes quiescent cell proline dipeptidase (QPP), DPP8, and DPP9 [see G. Lankas, et al., "Dipeptidyl Peptidase-IV Inhibition for the Treatment of Type 2 Diabetes: Potential Importance of Selectivity Over Dipeptidyl Peptidases 8 and 9," *Diabetes*, 54: 2988-2994 (2005); N. S. Kang, et al., "Docking-based 3D-QSAR study for selectivity of DPP4, DPP8, and DPP9 inhibitors," *Bioorg. Med. Chem. Lett.*, 17: 3716-3721 (2007)].

The therapeutic potential of DPP-4 inhibitors for the treatment of Type 2 diabetes is discussed by (i) D. J. Drucker, *Exp. Opin. Invest. Drugs*, 12: 87-100 (2003); (ii) K. Augustyns, et al., *Exp. Opin. Ther. Patents*, 13: 499-510 (2003); (iii) J. J. Hoist, *Exp. Opin. Emerg. Drugs*, 9: 155-166 (2004); (iv) H.-U. Demuth, et al., *Biochim. Biophys. Acta*, 1751: 33-44 (2005); (v) R. Mentlein, *Exp. Opin. Invest. Drugs*, 14: 57-64 (2005); (vi) K. Augustyns, "Inhibitors of proline-specific dipeptidyl peptidases: DPP IV inhibitors as a novel approach for the treatment of Type 2 diabetes," *Exp. Opin. Ther. Patents*, 15: 1387-1407 (2005); (vii) D. J. Drucker and M. A. Nauck, "The incretin system: GLP-1 receptor agonists and dipeptidyl peptidase-4 inhibitors in Type 2 diabetes," *The Lancet*, 368: 1696-1705 (2006); (viii) T. W. von Geldern and J. M. Trevillyan, "The Next Big Thing" in Diabetes: Clinical Progress on DPP-IV Inhibitors," *Drug Dev. Res.*, 67: 627-642 (2006); (ix) B. D. Green et al., "Inhibition of dipeptidyl peptidase IV activity as a therapy of Type 2 diabetes," *Exp. Opin. Emerging Drugs*, 11: 525-539 (2006); (x) J. J. Hoist and C. F. Deacon, "New Horizons in Diabetes Therapy," *Immun., Endoc. & Metab. Agents in Med. Chem.*, 7: 49-55 (2007); (xi) R. K. Campbell, "Rationale for Dipeptidyl Peptidase 4 Inhibitors: a New Class of Oral Agents for the Treatment of Type 2 Diabetes Mellitus," *Ann. Pharmacother.*, 41: 51-60 (2007); (xii) Z. Pei, "From the bench to the bedside: Dipeptidyl peptidase IV inhibitors, a new class of oral antihyperglycemic agents," *Curr. Opin. Drug Discovery Development*, 11: 512-532 (2008); and (xiii) J. J. Hoist, et al., "Glucagon-like peptide-1, glucose homeostasis, and diabetes, *Trends in Molecular Medicine*, 14: 161-168 (2008). Specific DPP-4 inhibitors either already approved or under clinical investigation for the treatment of Type 2 diabetes include sitagliptin, vildagliptin, saxagliptin, alogliptin, carmegliptin, melogliptin, and dutogliptin.

SUMMARY OF THE INVENTION

A compound of structural formula I:

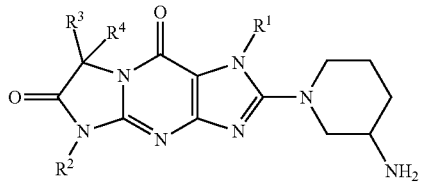

or a pharmaceutically acceptable salts thereof; wherein $R^1$, $R^2$, $R^3$ and $R^4$ are defined herein.

Also described herein are tricyclic heterocyclic compounds of the formulas described herein which are inhibitors of the dipeptidyl peptidase-IV enzyme ("DPP-4 inhibitors") and which are useful in the treatment of diseases in which the dipeptidyl peptidase-1V enzyme is involved, such as diabetes and particularly Type 2 diabetes. The invention is also directed to pharmaceutical compositions comprising these compounds and the use of these compounds and compositions in the treatment of such diseases in which the dipeptidyl peptidase-IV enzyme is involved.

DETAILED DESCRIPTION OF THE INVENTION

Compounds

A compound of structural formula I:

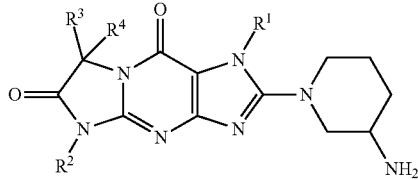

or a pharmaceutically acceptable salts thereof; wherein $R^1$ is selected from the group consisting of $C_1$-$C_6$alkyl, $C_2$-$C_6$alkenyl, $C_2$-$C_6$alkynyl, $C_3$-$C_{10}$cycloalkyl and benzyl; wherein the $C_1$-$C_6$alkyl, $C_2$-$C_6$alkenyl, $C_2$-$C_6$alkynyl, $C_3$-$C_{10}$cycloalkyl and benzyl are unsubstituted or substituted with 1-3 substituents each independently selected from $R^5$;

$R^2$, $R^3$ and $R^4$ are independently selected from the group consisting of hydrogen and $C_1$-$C_6$ alkyl wherein the $C_1$-$C_6$ alkyl is unsubstituted or substituted with one or more substituents selected from $R^5$; and $R^5$ is selected from the group consisting of hydrogen, halogen, $C_1$-$C_6$alkyl, halogen-substituted$C_1$-$C_6$alkyl, —OH, $C_1$-$C_6$alkylOH, halogen-substituted$C_1$-$C_6$alkylOH, —O$C_1$-$C_6$alkyl, -Ohalogen-substituted$C_1$-$C_6$alkyl, —COOH, —COO$C_1$-$C_6$alkyl, —$C_1$-$C_6$alkylCOO$C_1$-$C_6$alkyl, —$C_1$-$C_6$alkylCOOH, —O$C_1$-$C_6$alkylCOOH, —CN, $C_1$-$C_6$alkylCN, NH$_2$, NH$C_1$-$C_6$alkyl, N($C_1$-$C_6$alkyl)$_2$, —NHCOO$C_1$-$C_6$alkyl, $C_1$-$C_6$alkylCONH$_2$, —CONH$_2$, —CONH$C_1$-$C_6$alkyl, —NHCO$C_1$-$C_6$alkyl, —CON($C_1$-$C_6$alkyl)$_2$, —NHSO$_2$$C_1$-$C_6$alkyl, SO$_2$aryl, —SO$_2$$C_1$-$C_6$alkyl, $C_1$-$C_6$alkyl SO$_2$$C_1$-$C_6$alkyl, aryl, —NHCOaryl, and —NHCOheterocycle.

In certain embodiments of the compounds described herein, $R^1$ is selected from the group consisting of $C_1$-$C_6$alkyl, $C_2$-$C_6$alkenyl, $C_2$-$C_6$alkynyl, $C_3$-$C_{10}$cycloalkyl and benzyl; wherein the $C_1$-$C_6$alkyl, $C_2$-$C_6$alkenyl and $C_2$-$C_6$alkynyl, $C_3$-$C_{10}$cycloalkyl and benzyl are unsubstituted or substituted with 1-3 substituents each independently selected $R^5$. In one embodiment, $R^1$ is $C_1$-$C_6$alkyl. Suitable $C_1$-$C_6$alkyls include methyl, ethyl, propyl, butyl, pentyl and hexyl. In one embodiment, $R^1$ is $C_2$-$C_6$alkenyl. Suitable $C_2$-$C_6$alkenyls include ethenyl, propenyl, n-butenyl, 2-butynyl, 3-methylbut-2-enyl and n-pentenyl. In one embodiment, $R^1$ is $C_2$-$C_6$alkynyl. Suitable $C_2$-$C_6$alkynyls include ethynyl, propynyl, 2-propynyl, 2-butynyl and 3-methylbutynyl. For example in one embodiment, $R^1$ is 2-butynyl. In one embodiment, $R^1$ is $C_3$-$C_{10}$cycloalkyl. Suitable $C_3$-$C_{10}$cycloalkyls include cyclopropyl, cyclobutyl, cyclopentyl, cyclohexyl, cycloheptyl, cyclopentenyl, cyclohexenyl and cyclooctyl.

In certain embodiments, $R^1$ is unsubstituted. In another embodiment, $R^1$ is substituted with 1-3 substituents from selected from $R^5$. In one embodiment $R^1$ is substituted with 1 substituent selected from $R^5$. In one embodiment $R^1$ is substituted with 2 substituents selected from $R^5$. In one embodiment $R^1$ is substituted with 3 substituents selected from $R^5$. In another embodiment, $R^1$ is benzyl, wherein the benzyl is unsubstituted or substituted with 1-3 substituents each independently selected from $R^5$.

In another embodiment, $R^1$ is selected from the group consisting of is selected from the group consisting of methyl, benzyl, 2-fluorobenzyl, 2-butenyl, 2-butynyl, 2-propenyl, benzyl, 2,5-difluorobenzyl, 2,4,5-trifluorobenzyl, 2-cyanobenzyl, 2-cyano-5-fluorobenzyl, 2-cyano-4,5-difluorobenzyl, 2,4-dichlorobenzyl, and 2,5-dichlorobenzyl, wherein the methyl, 2-butynyl and benzyl are unsubstituted or substituted with 1-3 substituents selected from $R^5$. For example, in certain embodiments, $R^1$ is selected from the group consisting of 2-butynyl, 2-butenyl and benzyl, wherein the benzyl is unsubstituted or substituted with 1-3 substituents selected from the group $R^5$. In some embodiments, $R^1$ is selected from the group consisting of 2-butynyl, 2,5-difluorobenzyl, 3-methyl-2-butenyl, 3-fluorobenzyl, benzyl, methyl and 2-cyano-5-fluorobenzyl.

In yet another embodiment, $R^1$ is selected from the group consisting of methyl, 2-butynyl and benzyl, wherein the benzyl is unsubstituted or substituted with 1-3 substituents selected from the group $R^5$. For example, $R^1$ is benzyl, wherein the benzyl is substituted with two substituents independently selected from trifluoromethyl, fluoro and —CN.

In certain embodiments of the compounds described herein $R^2$, $R^3$ and $R^4$ are independently selected from the group consisting of hydrogen and $C_1$-$C_6$ alkyl wherein the $C_1$-$C_6$ alkyl is unsubstituted or substituted with one or more substituents selected from $R^5$.

In one embodiment $R^2$ is substituted with 1 substituent selected from $R^5$. In one embodiment $R^2$ is substituted with 2 substituents selected from $R^5$. In one embodiment $R^2$ is substituted with 3 substituents selected from $R^5$. In one embodiment $R^2$ is substituted with 1 substituent selected from $R^5$. In one embodiment $R^3$ is substituted with 2 substituents selected from $R^5$. In one embodiment $R^3$ is substituted with 3 substituents selected from $R^5$. In one embodiment $R^4$ is substituted with 1 substituent selected from $R^5$. In one embodiment $R^4$ is substituted with 2 substituents selected from $R^5$. In one embodiment $R^4$ is substituted with 3 substituents selected from $R^5$.

In one embodiment, $R^2$ is hydrogen. In another embodiment, $R^2$ is $C_1$-$C_6$ alkyl. Suitable $C_1$-$C_6$ alkyls include methyl, ethyl, propyl, butyl and hexyl. In one embodiment, $R^3$ is hydrogen. In another embodiment, $R^3$ is $C_1$-$C_6$ alkyl. Suitable $C_1$-$C_6$ alkyls include methyl, ethyl, propyl, butyl and hexyl. In one embodiment, $R^4$ is hydrogen. In another embodiment, $R^4$ is $C_1$-$C_6$ alkyl. Suitable $C_1$-$C_6$ alkyls include methyl, ethyl, propyl, butyl and hexyl.

In certain embodiments of the compounds described herein, $R^5$ is selected from the group consisting of hydrogen, halogen, $C_1$-$C_6$alkyl, halogen-substituted$C_1$-$C_6$alkyl, —OH, $C_1$-$C_6$alkylOH, halogen-substituted$C_1$-$C_6$alkylOH, —O$C_1$-$C_6$alkyl, -Ohalogen-substituted$C_1$-$C_6$alkyl, —COOH, —COO$C_1$-$C_6$alkyl, —$C_1$-$C_6$alkylCOO$C_1$-$C_6$alkyl, —$C_1$-$C_6$alkylCOOH, —O$C_1$-$C_6$alkylCOOH, —CN, $C_1$-$C_6$alkylCN, $NH_2$, $NHC_1$-$C_6$alkyl, $N(C_1$-$C_6$alkyl$)_2$, —NHCOO$C_1$-$C_6$alkyl, $C_1$-$C_6$alkylCONH$_2$, —CONH$_2$, —CONH$C_1$-$C_6$alkyl, —NHCO$C_1$-$C_6$alkyl, —CON($C_1$-$C_6$alkyl$)_2$, —NHSO$_2C_1$-$C_6$alkyl, SO$_2$aryl, —SO$_2C_1$-$C_6$alkyl, $C_1$-$C_6$alkyl SO$_2C_1$-$C_6$alkyl, aryl, —NHCOaryl, and -HCOheterocycle.

For example, in one embodiment $R^5$ is hydrogen. In another embodiment, $R^5$ is halogen. Suitable halogens include chlorine, fluorine, bromine and iodine. In yet another embodiment, $R^5$ is $C_1$-$C_6$alkyl. Suitable $C_1$-$C_6$alkyls include methyl, ethyl, propyl and butyl. In yet another embodiment, $R^5$ is halogen-substituted$C_1$-$C_6$alkyl. Suitable halogen-substituted$C_1$-$C_6$alkyls include fluoromethyl, difluoromethyl and trifluoromethyl. In still another embodiment, $R^5$ is —OH, $C_1$-$C_6$alkylOH or halogen-substituted$C_1$-$C_6$alkylOH. In another embodiment, $R^5$ is —O$C_1$-$C_6$alkyl and -Ohalogen-substituted$C_1$-$C_6$alkyl. Suitable examples include methoxy and trifluoromethoxy.

In still other embodiments of the compounds described herein, $R^5$ is —COOH, —COO$C_1$-$C_6$alkyl, —$C_1$-$C_6$alkylCOO$C_1$-$C_6$alkyl, —$C_1$-$C_6$alkylCOOH or —O$C_1$-$C_6$alkylCOOH. In another embodiment, $R^5$ is —CN. In yet another embodiment, $R^5$ is $C_1$-$C_6$alkylCN. In other embodiments, $R^5$ is $NH_2$, $NHC_1$-$C_6$alkyl or $N(C_1$-$C_6$alkyl$)_2$. In still other embodiments, $R^5$ is —NHCOO$C_1$-$C_6$alkyl. In yet other embodiments, $R^5$ is $C_1$-$C_6$alkylCONH$_2$, —CONH$_2$, —CONH$C_1$-$C_6$alkyl, —NHCO$C_1$-$C_6$alkyl or —CON($C_1$-$C_6$alkyl$)_2$. In another embodiment, $R^5$ is NHSO$_2C_1$-$C_6$alkyl, SO$_2$aryl, wherein the aryl is phenyl or napthyl, $C_1$-$C_6$alkylSO$_2C_1$-$C_6$alkyl or —SO$_2C_1$-$C_6$alkyl.

In certain embodiments of the compounds described herein, $R^5$ is aryl, wherein the aryl is phenyl or napthyl. In other embodiments, $R^5$ is —NHCOaryl or —NHCOheterocycle, wherein the aryl is phenyl or napthyl and the heterocycle is pyrrolyl, thienyl, imidazolyl, pyrazolyl, thiazolyl, isothiazolyl, oxazolyl, isoxazolyl, triazolyl, tetrazolyl, oxadiazolyl, 1,2,3-thiadiazolyl, 1,2,4-thiadiazolyl, 1,3,4-thiadiazolyl, pyridyl, pyrazinyl, pyrimidinyl, pyridazinyl, 1,2,4-triazinyl, 1,3,5-triazinyl, indolyl, benzothienyl, benzimidazolyl, benzopyrazolyl, benzoxazolyl, benzisoxazolyl, benzothiazolyl, benzisothiazolyl, indazolyl.

In certain embodiments of the compounds described herein, $R^5$ is selected from the group consisting of trifluoromethyl, halogen and —CN.

Embodiments of the compounds described herein include, but are not limited to:

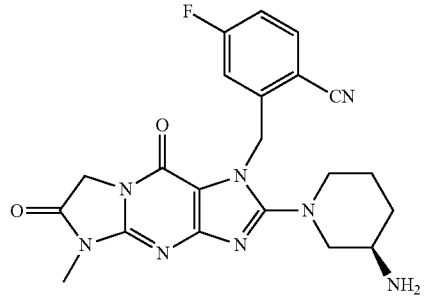 [SMILES: CN1C(=O)Cn2c1nc1nc(N3CCC[C@@H](N)C3)n(Cc3cc(F)ccc3C(F)(F)F)c1c2=O]

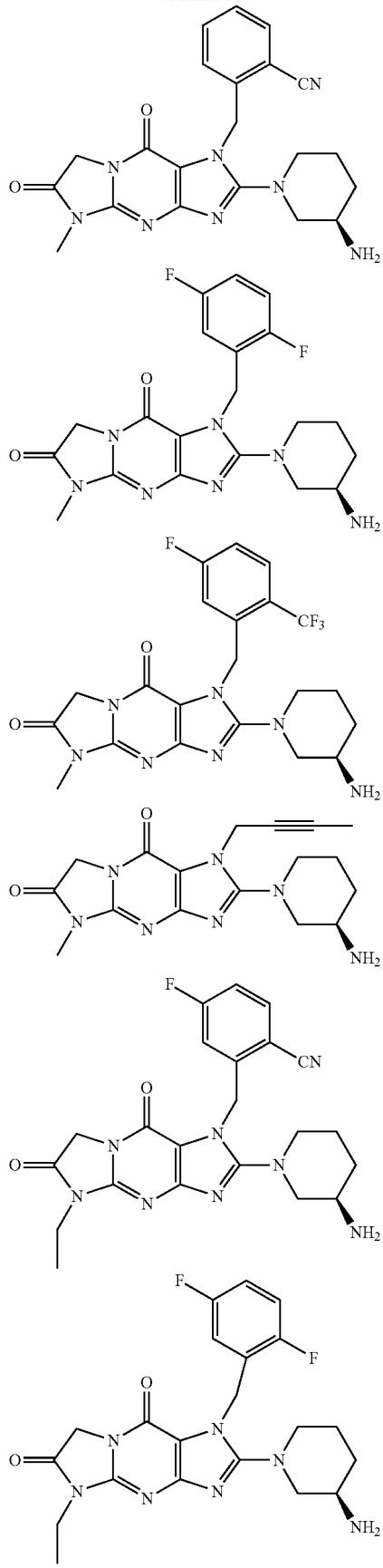

Definitions

As used herein the following definitions are applicable.

Examples of "halogen" include a fluorine atom, a chlorine atom, a bromine atom, and an iodine atom.

The term "$C_1$-$C_6$alkyl" encompasses straight alkyl having a carbon number of 1 to 6 and branched alkyl having a carbon number of 3 to 6. Specific examples thereof include methyl, ethyl, n-propyl, isopropyl, n-butyl, isobutyl, sec-butyl, tert-butyl, n-pentyl, isopentyl, neopentyl, tert-pentyl, 1-methylbutyl, 2-methylbutyl, 1,2-dimethylpropyl, 1-ethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1-ethylbutyl, 1,1,2-trimethylpropyl, 1,2,2-trimethylpropyl, 1-ethyl-2-methylpropyl, 1-ethyl-1-methylpropyl, and the like.

The term "halogen-substituted$C_1$-$C_6$ alkyl" encompasses $C_1$-$C_6$ alkyl with the hydrogen atoms thereof being partially or completely substituted with halogen, examples thereof including fluoromethyl, difluoromethyl, trifluoromethyl, 2-fluoroethyl, 1,2-difluoroethyl, 2,2-difluoroethyl and the like.

The term "$C_2$-$C_6$alkenyl" as used herein, refers to an aliphatic hydrocarbon group containing at least one carbon-carbon double bond and may be straight or branched and contains from about 2 to about 6 carbon atoms. Non-limiting examples of alkenyl groups include ethenyl, propenyl, n-butenyl, 3-methylbut-2-enyl and n-pentenyl.

The term "$C_2$-$C_6$alkynyl," as used herein, refers to an aliphatic hydrocarbon group containing at least one carbon-carbon triple bond and which may be straight or branched and contains from about 2 to about 6 carbon atoms. In one embodiment, an alkynyl group contains from about 2 to about 12 carbon atoms. In another embodiment, an alkynyl group contains from about 2 to about 6 carbon atoms. Non-limiting examples of alkynyl groups include ethynyl, propynyl, 2-butynyl and 3-methylbutynyl.

The term "aryl," as used herein, refers to an aromatic monocyclic or multicyclic ring system comprising from about 6 to about 14 carbon atoms. In one embodiment, an aryl group contains from about 6 to about 10 carbon atoms. An aryl group can be optionally substituted with one or more "ring system substituents" which may be the same or different, and are as defined herein below. Non-limiting examples of aryl groups include phenyl and naphthyl. In one embodiment, an aryl group is unsubstituted. In another embodiment, an aryl group is phenyl.

The term "$C_3$-$C_{10}$cycloalkyl," as used herein, refers to a monocyclic or polycyclic, saturated cycloalkyls having from 3 to 10 carbon atoms. Non-limiting examples of monocyclic cycloalkyls include cyclopropyl, cyclobutyl, cyclopentyl, cyclohexyl, cycloheptyl, cyclopentenyl, cyclohexenyl and cyclooctyl. Non-limiting examples of multicyclic cycloalkyls include 1-decalinyl, norbornyl and adamantyl. In one embodiment, a cycloalkyl group is unsubstituted.

The term "-Ohalogen-substituted$C_1$-$C_6$alkyl" means a —O$C_1$-$C_6$alkyl as defined above, which is substituted with 1-3 halogen atoms which are identical or different, and specifically includes, for example, a trifluoromethoxy group.

The term "$C_1$-$C_6$alkylOH" means a $C_1$-$C_6$alkyl substituted with an alcohol (—OH). Examples include methanol, propanol, butanol and t-butanol.

The term "halogen-substituted $C_1$-$C_6$alkylOH" means a halogen-substitued$C_1$-$C_6$alkyl substituted with an alcohol (—OH).

The term "COO$C_1$-$C_6$alkyl" means a —COOH group wherein the —OH is replaced with an alkoxy group as defined above. Examples include methoxycarbonyl, ethoxycarbonyl and butoxycarbonyl.

The term "$C_1$-$C_6$alkylCOOH" means a $C_1$-$C_6$alkyl substituted with a caboxcylic acid (COOH).

The term "O$C_1$-$C_6$alkylCOOH" means alkoxy substituted with a caboxcylic acid (COOH).

The term "$C_1$-$C_6$alkylCN" means a $C_1$-$C_6$alkyl substituted with a cyano group (—CN).

The term "NH$C_1$-$C_6$alkyl" means a group with one of the hydrogen atoms of amino (—$NH_2$) being substituted with a $C_{1-6}$ alkyl group. Specific examples thereof include methylamino, ethylamino, n-propylamino, isopropylamino, n-butylamino, sec-butylamino, tert-butylamino, and the like.

The term "N($C_1$-$C_6$alkyl)$_2$" means a group with the two amino hydrogen atoms each being substituted with a $C_{1-6}$ alkyl group. Specific examples thereof include dimethylamino, diethylamino, ethylmethylamino, di(n-propyl)amino, methyl(n-propyl)amino, diisopropylamino, and the like.

The term "$SO_2C_1$-$C_6$alkyl" means a group having $C_1$-$C_6$alkyl bonded to sulfonyl (—$SO_2$—). Specific examples thereof include methanesulfonyl, ethanesulfonyl, n-propanesulfonyl, isopropanesulfonyl, n-butanesulfonyl, sec-butanesulfonyl, tert-butanesulfonyl, and the like.

The term "CONH$C_1$-$C_6$alkyl" means a group with one of the hydrogen atoms of carbamoyl (—$CONH_2$) being substituted with $C_{1-6}$ alkyl. Specific examples thereof include methylcarbamoyl, ethylcarbamoyl, n-propylcarbamoyl, isopropylcarbamoyl, n-butylcarbamoyl, sec-butylcarbamoyl, tert-butylcarbamoyl, and the like.

The term "CON($C_1$-$C_6$alkyl)$_2$" means a group with the two carbamoyl hydrogen atoms each being substituted with $C_{1-6}$ alkyl. Specific examples thereof include dimethylcarbamoyl, diethylcarbamoyl, ethylmethylcarbamoyl, di(n-propyl)carbamoyl, methyl(n-propyl)carbamoyl, diisopropylcarbamoyl, and the like.

The term "NH$SO_2C_1$-$C_6$alkyl" means a group with one of the amino hydrogen atoms being substituted with $C_{1-6}$ alkylsulfonyl. Specific examples thereof include methanesulfonylamino, ethanesulfonylamino, n-propanesulfonylamino, isopropanesulfonylamino, n-butanesulfonylamino, sec-butanesulfonylamino, tert-butanesulfonylamino, and the like.

The term "NH$CO_2C_1$-$C_6$alkyl" means a group with one of the amino hydrogen atoms being substituted with $C_{1-6}$ alkoxycarbonyl and encompasses alkoxycarbonylamino having a carbon number of 1 to 6. Specific examples thereof include methoxycarbonylamino, ethoxycarbonylamino, n-propyloxycarbonylamino, isopropyloxycarbonylamino, n-butoxycarbonylamino, isobutoxycarbonylamino, tert-butoxycarbonylamino, n-pentyloxycarbonylamino, and the like.

The term "NHCO$C_1$-$C_6$alkyl" means a group with one of the amino hydrogen atoms being substituted with $C_{1-6}$alkylcarbonyl and encompasses alkylcarbonylamino having a carbon number of 1 to 6. Specific examples thereof include methylcarbonylamino, ethylcarbonylamino, n-propylcarbonylamino, isopropylcarbonylamino, n-butylcarbonylamino, isobutylcarbonylamino, tert-butylcarbonylamino, n-pentylcarbonylamino, and the like.

The term "heterocycle" means a saturated, partially-unsaturated or aromatic mono or multicyclic ring containing one or more, preferably one to three, same or different heteroatoms preferably selected from the group consisting of a nitrogen atom, an oxygen atom and a sulfur atom. Examples thereof include pyrrolyl, pyridyl, pyrazinyl, furanyl, thienyl, pyrimidinyl, pyridone (including N-substituted pyridones), isoxazolyl, oxetanyl, isothiazolyl, oxazolyl, oxadiazolyl, 1,3,4-thiadiazolyl, isoxazolyl, thiazolyl, pyrazolyl, furazanyl, triazolyl, tetrazolyl, 1,2,3-thiadiazolyl, 1,2,4-thiadiazolyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, 1,3,5-triazinyl, indolyl, benzothiazolyl, benzopyrazolyl, benzoxazolyl, benzisoxazolyl, benzisothiazolyl, indazolyl, tetrahydropyranyl, pyrrolidinyl, piperidinyl, piperazinyl, dioxanyl, imidazolidinyl, 2,3-dihydrofuro(2,3-b)pyridyl, benzoxazinyl, benzoxazolinyl, dihydrophthalazinyl, isoindolinyl, benzoxazepinyl, 5,6-dihydroimidazo[2,1-b]thiazolyl, tetrahydroquinolinyl, morpholinyl, tetrahydroisoquinolinyl, dihydroindolyl, thiomorpholinyl, thiazolidinyl, tetrahydrofuranyl, tetrahydrothiophenyl, lactam, lactone, 1,2,3,4-tetrahydropyridinyl, 1,2-dihydropyridinyl, 1,4-dihydropyridinyl, 1,2,3,6-tetrahydropyridinyl, 1,4,5,6-tetrahydropyrimidinyl, 2-pyrrolinyl, 3-pyrrolinyl, 2-imidazolinyl, 2-pyrazolinyl, dihydroimidazolyl, dihydrooxazolyl, dihydrooxadiazolyl, dihydrothiazolyl, 3,4-dihydro-2H-pyranyl, dihydrofuranyl, fluoro-substituted dihydrofuranyl, 7-oxabicyclo[2.2.1]heptenyl, dihydrothiophenyl, dihydrothiopyranyl, and the like. The term also includes partially unsaturated monocyclic rings that are not aromatic, such as 2- or 4-pyridones attached through the nitrogen or N-substituted-(1H, 3H)-pyrimidine-2,4-diones (N-substituted uracils). The term also includes bridged rings such as 5-azabicyclo[2.2.1]heptyl, 2,5-diazabicyclo[2.2.1]heptyl, 2-azabicyclo[2.2.1]heptyl, 7-azabicyclo[2.2.1]heptyl, 2,5-diazabicyclo[2.2.2]octyl, 2-azabicyclo[2.2.2]octyl, and 3-azabicyclo[3.2.2]nonyl, and azabicyclo[2.2.1]heptanyl.

The compounds of the present invention contain one or more asymmetric centers and can thus occur as racemates, racemic mixtures, single enantiomers, diastereomeric mixtures, and individual diastereomers. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds.

Some of the compounds described herein contain olefinic double bonds, and unless specified otherwise, are meant to include both E and Z geometric isomers.

Some of the compounds described herein may exist as tautomers, which have different points of attachment of hydrogen accompanied by one or more double bond shifts. For example, a ketone and its enol form are keto-enol tautomers. The individual tautomers as well as mixtures thereof are encompassed with compounds of the present invention.

The independent syntheses of these diastereomers or their chromatographic separations may be achieved as known in the art by appropriate modification of the methodology disclosed herein. Their absolute stereochemistry may be determined by the X-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium (1H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

It will be understood that, as used herein, references to the compounds of structural Formula I are meant to also include the pharmaceutically acceptable salts, and also salts that are not pharmaceutically acceptable when they are used as precursors to the free compounds or their pharmaceutically acceptable salts or in other synthetic manipulations.

The compounds of the present invention may be administered in the form of a pharmaceutically acceptable salt. The term "pharmaceutically acceptable salt" refers to salts prepared from pharmaceutically acceptable non-toxic bases or acids including inorganic or organic bases and inorganic or organic acids. Salts of basic compounds encompassed within the term "pharmaceutically acceptable salt" refer to non-toxic salts of the compounds of this invention which are generally prepared by reacting the free base with a suitable organic or inorganic acid. Representative salts of basic compounds of the present invention include, but are not limited to, acetate, benzenesulfonate, benzoate, bicarbonate, bisulfate, bitartrate, borate, bromide, camsylate, carbonate, clavulanate, citrate, edetate, edisylate, estolate, esylate, fumarate, gluceptate, gluconate, glutamate, hexylresorcinate, hydrabamine, hydrobromide, hydrochloride, hydroxynaphthoate, iodide, isothionate, lactate, lactobionate, laurate, malate, maleate, mandelate, mesylate, methylbromide, methylsulfate, mucate, napsylate, nitrate, N-methylglucamine ammonium salt, oleate, oxalate, pamoate (embonate), palmitate, pantothenate, phosphate, polygalacturonate, salicylate, stearate, sulfate, subacetate, succinate, tannate, tartrate, teoclate, tosylate, triethiodide and valerate. Furthermore, where the compounds of the invention carry an acidic moiety, suitable pharmaceutically acceptable salts thereof include, but are not limited to, salts derived from inorganic bases including aluminum, ammonium, calcium, copper, ferric, ferrous, lithium, magnesium, manganic, mangamous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, cyclic amines, and basic ion-exchange resins, such as arginine, betaine, caffeine, choline, N,N-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

Also, in the case of a carboxylic acid (—COOH) or alcohol group being present in the compounds of the present invention, pharmaceutically acceptable esters of carboxylic acid derivatives, such as methyl, ethyl, or pivaloyloxymethyl, or acyl derivatives of alcohols, such as O-acetyl, O-pivaloyl, O-benzoyl, and O-aminoacyl, can be employed. Included are those esters and acyl groups known in the art for modifying the solubility or hydrolysis characteristics for use as sustained-release or prodrug formulations.

Solvates, and in particular, the hydrates of the compounds of structural Formula I are included in the present invention as well.

Methods of Treatment

The subject compounds are useful in a method of inhibiting the dipeptidyl peptidase-IV enzyme in a patient such as a mammal in need of such inhibition comprising the administration of an effective amount of the compound. The present invention is directed to the use of the compounds disclosed herein as inhibitors of dipeptidyl peptidase-IV enzyme activity.

In addition to primates, such as humans, a variety of other mammals can be treated according to the method of the present invention. For instance, mammals including, but not limited to, cows, sheep, goats, horses, dogs, cats, guinea pigs, rats or other bovine, ovine, equine, canine, feline, rodent or murine species can be treated. However, the method can also be practiced in other species, such as avian species (e.g., chickens).

The present invention is further directed to a method for the manufacture of a medicament for inhibiting dipeptidyl peptidase-IV enzyme activity in humans and animals comprising combining a compound of the present invention with a pharmaceutically acceptable carrier or diluent. More particularly, the present invention is directed to the use of a compound of structural Formula I in the manufacture of a medicament for use in treating a condition selected from the group consisting of hyperglycemia, Type 2 diabetes, obesity, and a lipid disorder in a mammal, wherein the lipid disorder is selected from the group consisting of dyslipidemia, hyperlipidemia, hypertriglyceridemia, hypercholesterolemia, low HDL, and high LDL.

The subject treated in the present methods is generally a mammal, preferably a human being, male or female, in whom inhibition of dipeptidyl peptidase-IV enzyme activity is desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising the specified ingredients in the specified amounts, as well as any product which results, directly or indirectly, from combination of the specified ingredients in the specified amounts. Such term in relation to pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier. By "pharmaceutically acceptable" it is meant the carrier, diluent or excipient must be compatible with the other ingredients of the formulation and not deleterious to the recipient thereof.

The terms "administration of" and or "administering a" compound should be understood to mean providing a compound of the invention or a prodrug of a compound of the invention to the individual in need of treatment.

Dipeptidyl peptidase-IV enzyme (DPP-4) is a cell surface protein that has been implicated in a wide range of biological functions. It has a broad tissue distribution (intestine, kidney, liver, pancreas, placenta, thymus, spleen, epithelial cells, vascular endothelium, lymphoid and myeloid cells, serum), and distinct tissue and cell-type expression levels. DPP-4 is identical to the T cell activation marker CD26, and it can cleave a number of immunoregulatory, endocrine, and neurological peptides in vitro. This has suggested a potential role for this peptidase in a variety of disease processes in humans or other species.

Accordingly, the subject compounds are useful in a method for the prevention or treatment of the following diseases, disorders and conditions:

Type II Diabetes and Related Disorders: It is well established that the incretins GLP-1 and GIP are rapidly inactivated in vivo by DPP-4. Studies with DPP-4$^{(-/-)}$-deficient mice and preliminary clinical trials indicate that DPP-4 inhibition increases the steady state concentrations of GLP-1 and GIP, resulting in improved glucose tolerance. By analogy to GLP-1 and GIP, it is likely that other glucagon family peptides involved in glucose regulation are also inactivated by DPP-4 (eg. PACAP). Inactivation of these peptides by DPP-4 may also play a role in glucose homeostasis. The DPP-4 inhibitors of the present invention therefore have utility in the treatment of type II diabetes and in the treatment and prevention of the numerous conditions that often accompany Type II diabetes, including Syndrome X (also known as Metabolic Syndrome), reactive hypoglycemia, and diabetic dyslipidemia. Obesity, discussed below, is another condition that is often found with Type II diabetes that may respond to treatment with the compounds of this invention.

The following diseases, disorders and conditions are related to Type 2 diabetes, and therefore may be treated, controlled or in some cases prevented, by treatment with the compounds of this invention: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), and other disorders where insulin resistance is a component. In Syndrome X, also known as Metabolic Syndrome, obesity is thought to promote insulin resistance, diabetes, dyslipidemia, hypertension, and increased cardiovascular risk. Therefore, DPP-4 inhibitors may also be useful to treat hypertension associated with this condition.

Obesity: DPP-4 inhibitors may be useful for the treatment of obesity. This is based on the observed inhibitory effects on food intake and gastric emptying of GLP-1 and GLP-2. Exogenous administration of GLP-1 in humans significantly decreases food intake and slows gastric emptying (*Am. J. Physiol.*, 277: R910-R916 (1999)). ICV administration of GLP-1 in rats and mice also has profound effects on food intake (*Nature Medicine*, 2: 1254-1258 (1996)). This inhibition of feeding is not observed in GLP-1R$^{(-/-)}$ mice, indicating that these effects are mediated through brain GLP-1 receptors. By analogy to GLP-1, it is likely that GLP-2 is also regulated by DPP-4. ICV administration of GLP-2 also inhibits food intake, analogous to the effects observed with GLP-1 (*Nature Medicine*, 6: 802-807 (2000)). In addition, studies with DPP-4 deficient mice suggest that these animals are resistant to diet-induced obesity and associated pathology (e.g. hyperinsulinonemia).

Cardiovascular Disease: GLP-1 has been shown to be beneficial when administered to patients following acute myocardial infarction, leading to improved left ventricular function and reduced mortality after primary angioplasty (Circulation, 109: 962-965 (2004)). GLP-1 administration is also useful for the treatment of left ventricular systolic dysfunction in dogs with dilated cardiomyopathy and ischemic induced left ventricular dysfunction, and thus may prove useful for the treatment of patients with heart failure (US2004/0097411). DPP-4 inhibitors are expected to show similar effects through their ability to stabilize endogenous GLP-1.

Growth Hormone Deficiency: DPP-4 inhibition may be useful for the treatment of growth hormone deficiency, based on the hypothesis that growth-hormone releasing factor (GRF), a peptide that stimulates release of growth hormone from the anterior pituitary, is cleaved by the DPP-4 enzyme in vivo (WO 00/56297). The following data provide evidence that GRF is an endogenous substrate: (1) GRF is efficiently cleaved in vitro to generate the inactive product GRF[3-44] (*BBA* 1122: 147-153 (1992)); (2) GRF is rapidly degraded in plasma to GRF[3-44]; this is prevented by the DPP-4 inhibitor diprotin A; and (3) GRF[3-44] is found in the plasma of a human GRF transgenic pig (*J. Clin. Invest.*, 83: 1533-1540 (1989)). Thus DPP-4 inhibitors may be useful for the same spectrum of indications which have been considered for growth hormone secretagogues.

Intestinal Injury: The potential for using DPP-4 inhibitors for the treatment of intestinal injury is suggested by the results of studies indicating that glucagon-like peptide-2 (GLP-2), a likely endogenous substrate for DPP-4, may exhibit trophic effects on the intestinal epithelium (*Regulatory Peptides*, 90: 27-32 (2000)). Administration of GLP-2 results in increased small bowel mass in rodents and attenuates intestinal injury in rodent models of colitis and enteritis.

Immunosuppression: DPP-4 inhibition may be useful for modulation of the immune response, based upon studies implicating the DPP-4 enzyme in T cell activation and in chemokine processing, and efficacy of DPP-4 inhibitors in in vivo models of disease. DPP-4 has been shown to be identical to CD26, a cell surface marker for activated immune cells. The expression of CD26 is regulated by the differentiation and activation status of immune cells. It is generally accepted that CD26 functions as a co-stimulatory molecule in in vitro models of T cell activation. A number of chemokines contain proline in the penultimate position, presumably to protect them from degradation by non-specific aminopeptidases. Many of these have been shown to be processed in vitro by DPP-4. In several cases (RANTES, LD78-beta, MDC, eotaxin, SDF-1alpha), cleavage results in an altered activity in chemotaxis and signaling assays. Receptor selectivity also appears to be modified in some cases (RANTES). Multiple N-terminally truncated forms of a number of chemokines have been identified in in vitro cell culture systems, including the predicted products of DPP-4 hydrolysis.

DPP-4 inhibitors have been shown to be efficacious immunosuppressants in animal models of transplantation and arthritis. Prodipine (Pro-Pro-diphenyl-phosphonate), an irreversible inhibitor of DPP-4, was shown to double cardiac allograft survival in rats from day 7 to day 14 (*Transplantation*, 63: 1495-1500 (1997)). DPP-4 inhibitors have been tested in collagen and alkyldiamine-induced arthritis in rats and showed a statistically significant attenuation of hind paw swelling in this model [*Int. J. Immunopharmacology*, 19:15-24 (1997) and *Immunopharmacology*, 40: 21-26 (1998)]. DPP-4 is upregulated in a number of autoimmune diseases including rheumatoid arthritis, multiple sclerosis, Graves' disease, and Hashimoto's thyroiditis (*Immunology Today*, 20: 367-375 (1999)).

HIV Infection: DPP-4 inhibition may be useful for the treatment or prevention of HIV infection or AIDS because a number of chemokines which inhibit HIV cell entry are potential substrates for DPP-4 (*Immunology Today* 20: 367-375 (1999)). In the case of SDF-1alpha, cleavage decreases antiviral activity (*PNAS*, 95: 6331-6 (1998)). Thus, stabilization of SDF-1alpha through inhibition of DPP-4 would be expected to decrease HIV infectivity.

Hematopoiesis: DPP-4 inhibition may be useful for the treatment or prevention of hematopiesis because DPP-4 may be involved in hematopoiesis. A DPP-4 inhibitor, Val-Boro-Pro, stimulated hematopoiesis in a mouse model of cyclophosphamide-induced neutropenia (WO 99/56753).

Neuronal Disorders: DPP-4 inhibition may be useful for the treatment or prevention of various neuronal or psychiatric disorders because a number of peptides implicated in a variety of neuronal processes are cleaved in vitro by DPP-4. A DPP-4 inhibitor thus may have a therapeutic benefit in the treatment of neuronal disorders. Endomorphin-2, beta-casomorphin, and substance P have all been shown to be in vitro substrates for DPP-4. In all cases, in vitro cleavage is highly efficient, with $k_{cat}/K_m$ about $10^6$ $M^{-1}s^{-1}$ or greater. In an electric shock jump test model of analgesia in rats, a DPP-4 inhibitor showed a significant effect that was independent of the presence of exogenous endomorphin-2 (*Brain Research*, 815: 278-286 (1999)). Neuroprotective and neuroregenerative effects of DPP-4 inhibitors were also evidenced by the inhibitors' ability to protect motor neurons from excitotoxic cell death, to protect striatal innervation of dopaminergic neurons when administered concurrently with MPTP, and to promote recovery of striatal innervation density when given in a therapeutic manner following MPTP treatment [see Yong-Q. Wu, et al., "Neuroprotective Effects of Inhibitors of Dipeptidyl peptidase-IV In Vitro and In Vivo," *Int. Conf. On Dipeptidyl Aminopeptidases: Basic Science and Clinical Applications*, Sep. 26-29, 2002 (Berlin, Germany)].

Anxiety: Rats naturally deficient in DPP-4 have an anxiolytic phenotype (WO 02/34243; Karl et al., *Physiol. Behav.* 2003). DPP-4 deficient mice also have an anxiolytic phenotype using the porsolt and light/dark models. Thus DPP-4 inhibitors may prove useful for treating anxiety and related disorders.

Memory and Cognition: GLP-1 agonists are active in models of learning (passive avoidance, Morris water maze) and neuronal injury (kainate-induced neuronal apoptosis) as demonstrated by During et al. (*Nature Med.* 9: 1173-1179 (2003)). The results suggest a physiological role for GLP-1 in learning and neuroprotection. Stabilization of GLP-1 by DPP-4 inhibitors are expected to show similar effects Myocardial Infarction: GLP-1 has been shown to be beneficial when administered to patients following acute myocardial infarction (Circulation, 109: 962-965 (2004)). DPP-4 inhibitors are expected to show similar effects through their ability to stabilize endogenous GLP-1.

Tumor Invasion and Metastasis: DPP-4 inhibition may be useful for the treatment or prevention of tumor invasion and metastasis because an increase or decrease in expression of several ectopeptidases including DPP-4 has been observed during the transformation of normal cells to a malignant phenotype (*J. Exp. Med.*, 190: 301-305 (1999)). Up- or down-regulation of these proteins appears to be tissue and cell-type specific. For example, increased CD26/DPP-4 expression has been observed on T cell lymphoma, T cell acute lymphoblastic leukemia, cell-derived thyroid carcinomas, basal cell carcinomas, and breast carcinomas. Thus, DPP-4 inhibitors may have utility in the treatment of such carcinomas.

Benign Prostatic Hypertrophy: DPP-4 inhibition may be useful for the treatment of benign prostatic hypertrophy because increased DPP-4 activity was noted in prostate tissue from patients with BPH (*Eur. J. Clin. Chem. Clin. Biochem.*, 30: 333-338 (1992)).

Sperm Motility/Male Contraception: DPP-4 inhibition may be useful for the altering sperm motility and for male contraception because in seminal fluid, prostatosomes, prostate derived organelles important for sperm motility, possess very high levels of DPP-4 activity (*Eur. J. Clin. Chem. Clin. Biochem.*, 30: 333-338 (1992)).

Gingivitis: DPP-4 inhibition may be useful for the treatment of gingivitis because DPP-4 activity was found in gingival crevicular fluid and in some studies correlated with periodontal disease severity (*Arch. Oral Biol.*, 37: 167-173 (1992)).

Osteoporosis: DPP-4 inhibition may be useful for the treatment or prevention of osteoporosis because GIP receptors are present in osteoblasts.

Stem Cell Transplantation: Inhibition of DPP-4 on donor stem cells has been shown to lead to an enhancement of their bone marrow homing efficiency and engraftment, and an increase in survival in mice (Christopherson, et al., *Science*, 305:1000-1003 (2004)). Thus DPP-4 inhibitors may be useful in bone marrow transplantation.

The compounds of the present invention have utility in treating or preventing one or more of the following conditions or diseases: (1) hyperglycemia, (2) low glucose tolerance, (3) insulin resistance, (4) obesity, (5) lipid disorders, (6) dyslipidemia, (7) hyperlipidemia, (8) hypertriglyceridemia, (9) hypercholesterolemia, (10) low HDL levels, (11) high LDL levels, (12) atherosclerosis and its sequelae, (13) vascular restenosis, (14) irritable bowel syndrome, (15) inflammatory bowel disease, including Crohn's disease and ulcerative colitis, (16) other inflammatory conditions, (17) pancreatitis, (18) abdominal obesity, (19) neurodegenerative disease, (20) retinopathy, (21) nephropathy, (22) neuropathy, (23) Syndrome X, (24) ovarian hyperandrogenism (polycystic ovarian syndrome), (25) Type 2 diabetes, (26) growth hormone deficiency, (27) neutropenia, (28) neuronal disorders, (29) tumor metastasis, (30) benign prostatic hypertrophy, (32) gingivitis, (33) hypertension, (34) osteoporosis, (35) anxiety, (36) memory deficit, (37) cognition deficit, (38) stroke, (39) Alzheimer's disease, and other conditions that may be treated or prevented by inhibition of DPP-4.

The compounds of the present invention are further useful in methods for the prevention or treatment of the aforementioned diseases, disorders and conditions in combination with other therapeutic agents.

Combination Therapy

The compounds of the present invention may be used in combination with one or more other drugs in the treatment, prevention, suppression or amelioration of diseases or conditions for which compounds of Formula I or the other drugs may have utility, where the combination of the drugs together are safer or more effective than either drug alone. Such other drug(s) may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred, particularly in combination with a pharmaceutically acceptable carrier. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the second active ingredient may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, preferably about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s).

Examples of other active ingredients that may be administered in combination with a compound of Formula I, and either administered separately or in the same pharmaceutical composition, include, but are not limited to:

(1) insulin sensitizers, including (i) PPARγ agonists, such as the glitazones (e.g. pioglitazone, rosiglitazone, netoglitazone, rivoglitazone, and balaglitazone) and other PPAR ligands, including (1) PPARα/γ dual agonists, such as muraglitazar, aleglitazar, sodelglitazar, and naveglitazar, (2) PPARα agonists, such as fenofibric acid derivatives (gemfibrozil, clofibrate, ciprofibrate, fenofibrate and bezafibrate), (3) selective PPARγ modulators (SPPARγM's), such as those disclosed in WO 02/060388, WO 02/08188, WO 2004/019869, WO 2004/020409, WO 2004/020408, and WO 2004/066963, and (4) PPARγ partial agonists; (ii) biguanides, such as metformin and its pharmaceutically acceptable salts, in particular, metformin hydrochloride, and extended-release formulations thereof, such as Glumetza®, Fortamet®, and GlucophageXR®; (iii) protein tyrosine phosphatase-1B (PTP-1B) inhibitors;

(2) insulin and insulin analogs or derivatives, such as insulin lispro, insulin detemir, insulin glargine, insulin glulisine, and inhalable formulations of each thereof;

(3) leptin and leptin derivatives, agonists, and analogs, such as meterleptin;

(4) amylin; amylin analogs, such as davalintide; and amylin agonists, such as pramlintide;

(5) sulfonylurea and non-sulfonylurea insulin secretagogues, such as tolbutamide, glyburide, glipizide, glimepiride, mitiglinide, and meglitinides, such as nateglinide and repaglinide;

(6) α-glucosidase inhibitors (such as acarbose, voglibose and miglitol);

(7) glucagon receptor antagonists, such as those disclosed in WO 98/04528, WO 99/01423, WO 00/39088, and WO 00/69810;

(8) incretin mimetics, such as GLP-1, GLP-1 analogs, derivatives, and mimetics (See for example, WO 2008/011446, U.S. Pat. Nos. 5,545,618, 6,191,102, and No. 5,658, 3111); and GLP-1 receptor agonists, such as oxyntomodulin and its analogs and derivatives (See for example, WO 2003/022304, WO 2006/134340, WO 2007/100535), glucagon and its analogs and derivatives (See for example, WO 2008/101017), exenatide, liraglutide, taspoglutide, albiglutide, AVE0010, CJC-1134-PC, NN9535, LY2189265, LY2428757, and BIM-51077, including intranasal, transdermal, and once-weekly formulations thereof, such as exenatide QW;

(9) LDL cholesterol lowering agents such as (i) C (lovastatin, simvastatin, pravastatin, cerivastatin, fluvastatin, atorvastatin, pitavastatin, and rosuvastatin), (ii) bile acid sequestering agents (such as cholestyramine, colestimide, colesevelam hydrochloride, colestipol, and dialkylaminoalkyl derivatives of a cross-linked dextran, (iii) inhibitors of cholesterol absorption, such as ezetimibe, and (iv) acyl CoA:cholesterol acyltransferase inhibitors, such as avasimibe;

(10) HDL-raising drugs, such as niacin or a salt thereof and extended-release versions thereof; MK-524A, which is a combination of niacin extended-release and the DP-1 antagonist MK-524; and nicotinic acid receptor agonists;

(11) antiobesity compounds;

(12) agents intended for use in inflammatory conditions, such as aspirin, non-steroidal anti-inflammatory drugs (NSAIDs), glucocorticoids, and selective cyclooxygenase-2 (COX-2) inhibitors;

(13) antihypertensive agents, such as ACE inhibitors (such as enalapril, lisinopril, ramipril, captopril, quinapril, and tandolapril), A-II receptor blockers (such as losartan, candesartan, irbesartan, olmesartan medoxomil, valsartan, telmisartan, and eprosartan), renin inhibitors (such as aliskiren), beta blockers (such as and calcium channel blockers (such as;

(14) glucokinase activators (GKAs), such as LY2599506;

(15) inhibitors of 11β-hydroxysteroid dehydrogenase type 1, such as those disclosed in U.S. Pat. No. 6,730,690; WO 03/104207; and WO 04/058741;

(16) inhibitors of cholesteryl ester transfer protein (CETP), such as torcetrapib and MK-0859;

(17) inhibitors of fructose 1,6-bisphosphatase, such as those disclosed in U.S. Pat. Nos. 6,054,587; 6,110,903; 6,284,748; 6,399,782; and 6,489,476;

(18) inhibitors of acetyl CoA carboxylase-1 or 2 (ACC1 or ACC2);

(19) AMP-activated Protein Kinase (AMPK) activators;

(20) agonists of the G-protein-coupled receptors: GPR-109, GPR-116, GPR-119, and GPR-40;

(21) SSTR3 antagonists, such as those disclosed in WO 2009/011836;

(22) neuromedin U receptor 1 (NMUR1) and/or neuromedin U receptor 2 (NMUR2) agonists, such as those disclosed in WO2007/109135 and WO2009/042053, including, but not limited to, neuromedin U (NMU) and neuromedin S (NMS) and their analogs and derivatives;

(23) inhibitors of stearoyl-coenzyme A delta-9 desaturase (SCD);

(24) GPR-105 (P2YR14) antagonists, such as those disclosed in WO 2009/000087;

(25) inhibitors of glucose uptake, such as sodium-glucose transporter (SGLT) inhibitors and its various isoforms, such as SGLT-1; SGLT-2, such as dapagliflozin, LX-4211, canagliflozin, tofogliflozin, sergliflozin, BI-10773, PF-729, Ipragliflozin, AVE2268, and remogliflozin; and SGLT-3;

(26) inhibitors of acyl coenzyme A:diacylglycerol acyltransferase 1 and 2 (DGAT-1 and DGAT-2) such as PF-04620110 (Pfizer);

(27) inhibitors of fatty acid synthase;

(28) inhibitors of acyl coenzyme A:monoacylglycerol acyltransferase 1 and 2 (MGAT-1 and MGAT-2);

(29) agonists of the TGR5 receptor (also known as GPBAR1, BG37, GPCR19, GPR131, and M-BAR);

(30) bromocriptine mesylate and rapid-release formulations thereof;

(31) histamine H3 receptor agonists; and

(32) α2-adrenergic or β3-adrenergic receptor agonists.

Antiobesity compounds that can be combined with compounds of Formula I include topiramate; zonisamide; naltrexone; phentermine; bupropion; the combination of bupropion and naltrexone; the combination of bupropion and zonisamide; the combination of topiramate and phentermine; fenfluramine; dexfenfluramine; sibutramine; lipase inhibitors, such as orlistat and cetilistat; melanocortin receptor agonists, in particular, melanocortin-4 receptor agonists; CCK-1 agonists; melanin-concentrating hormone (MCH) receptor antagonists; neuropeptide Y1 or Y5 antagonists (such as MK-0557); CB1 receptor inverse agonists and antagonists (such as rimonabant and taranabant); β3 adrenergic receptor agonists; ghrelin antagonists; bombesin receptor agonists (such as bombesin receptor subtype-3 agonists); histamine H3 receptor inverse agonists; 5-hydroxytryptamine-2c (5-HT2c) agonists, such as lorcaserin; and inhibitors of fatty acid synthase (FAS). For a review of anti-obesity compounds that can be combined with compounds of the present invention, see S. Chaki et al., "Recent advances in feeding suppressing agents: potential therapeutic strategy for the treatment of obesity," *Expert Opin. Ther. Patents*, 11: 1677-1692 (2001); D. Spanswick and K. Lee, "Emerging antiobesity drugs," *Expert Opin. Emerging Drugs*, 8: 217-237 (2003); J. A. Fernandez-Lopez, et al., "Pharmacological Approaches for the Treatment of Obesity," *Drugs*, 62: 915-944 (2002); and K. M. Gadde, et al., "Combination pharmaceutical therapies for obesity," *Exp. Opin. Pharmacother.*, 10: 921-925 (2009).

Glucagon receptor antagonists that can be used in combination with the compounds of Formula I include, but are not limited to:

N-[4-((1S)-1-{3-(3,5-dichlorophenyl)-5-[6-(trifluoromethoxy)-2-naphthyl]-1H-pyrazol-1-yl}ethyl)benzoyl]-β-alanine;

N-[4-((1R)-1-{3-(3,5-dichlorophenyl)-5-[6-(trifluoromethoxy)-2-naphthyl]-1H-pyrazol-1-yl}ethyl)benzoyl]-β-alanine;

N-(4-{1-[3-(2,5-dichlorophenyl)-5-(6-methoxy-2-naphthyl)-1H-pyrazol-1-yl]ethyl}benzoyl)-β-alanine;

N-(4-{(1S)-1-[3-(3,5-dichlorophenyl)-5-(6-methoxy-2-naphthyl)-1H-pyrazol-1-yl]ethyl}benzoyl)-β-alanine;

N-(4-{(1S)-1-[(R)-(4-chlorophenyl)(7-fluoro-5-methyl-1H-indol-3-yl)methyl]butyl}benzoyl)-β-alanine; and N-(4-{(1S)-1-[(4-chlorophenyl)(6-chloro-8-methylquinolin-4-yl)methyl]butyl}benzoyl)-β-alanine; and pharmaceutically acceptable salts thereof.

Inhibitors of stearoyl-coenzyme A delta-9 desaturase (SCD) that can be used in combination with the compounds of Formula I include, but are not limited to:

[5-(5-{4-[2-(trifluoromethyl)phenoxy]piperidin-1-yl}-1,3,4-thiadiazol-2-yl)-2H-tetrazol-2-yl]acetic acid;

(2'-{4-[2-(trifluoromethyl)phenoxy]piperidin-1-yl}-2,5'-bi-1,3-thiazol-4-yl)acetic acid;

(5-{3-[4-(2-bromo-5-fluorophenoxy)piperidin-1-yl]isoxazol-5-yl}-2H-tetrazol-2-yl)acetic acid;

(3-{3-[4-(2-bromo-5-fluorophenoxy)piperidin-1-yl]-1,2,4-oxadiazol-5-yl}-1H-pyrrol-1-yl)acetic acid;

(5-{5-[4-(2-bromo-5-fluorophenoxy)piperidin-1-yl]pyrazin-2-yl}-2H-tetrazol-2-yl)acetic acid; and (5-{2-[4-(5-bromo-2-chlorophenoxy)piperidin-1-yl]pyrimidin-5-yl}-2H-tetrazol-2-yl)acetic acid; and pharmaceutically acceptable salts thereof.

Glucokinase activators that can be used in combination with the compounds of Formula I include, but are not limited to:

3-(6-ethanesulfonylpyridin-3-yloxy)-5-(2-hydroxy-1-methyl-ethoxy)-N-(1-methyl-1H-pyrazol-3-yl)benzamide;

5-(2-hydroxy-1-methyl-ethoxy)-3-(6-methanesulfonylpyridin-3-yloxy)-N-(1-methyl-1H-pyrazol-3-yl)benzamide;

5-(1-hydroxymethyl-propoxy)-3-(6-methanesulfonylpyridin-3-yloxy)-N-(1-methyl-1H-pyrazol-3-yl)benzamide;

3-(6-methanesulfonylpyridin-3-yloxy)-5-(1-methoxymethyl-propoxy)-N-(1-methyl-1H-pyrazol-3-yl)benzamide;

5-isopropoxy-3-(6-methanesulfonylpyridin-3-yloxy)-N-(1-methyl-1H-pyrazol-3-yl)benzamide;

5-(2-fluoro-1-fluoromethyl-ethoxy)-3-(6-methanesulfonylpyridin-3-yloxy)-N-(1-methyl-1H-pyrazol-3-yl)benzamide;

3-({4-[2-(dimethylamino)ethoxy]phenyl}thio)-N-(3-methyl-1,2,4-thiadiazol-5-yl)-6-[(4-methyl-4H-1,2,4-triazol-3-yl)thio]pyridine-2-carboxamide;

3-({4-[(1-methylazetidin-3-yl)oxy]phenyl}thio)-N-(3-methyl-1,2,4-thiadiazol-5-yl)-6-[(4-methyl-4H-1,2,4-triazol-3-yl)thio]pyridine-2-carboxamide;

N-(3-methyl-1,2,4-thiadiazol-5-yl)-6-[(4-methyl-4H-1,2,4-triazol-3-yl)thio]-3-{[4-(2-pyrrolidin-1-ylethoxy)phenyl]thio}pyridine-2-carboxamide; and
3-[(4-{2-[(2R)-2-methylpyrrolidin-1-yl]ethoxy}phenyl)thio-N-(3-methyl-1,2,4-thiadiazol-5-yl)-6-[(4-methyl-4H-1,2,4-triazol-3-yl)thio]pyridine-2-carboxamide; and
pharmaceutically acceptable salts thereof.

Agonists of the GPR-119 receptor that can be used in combination with the compounds of Formula I include, but are not limited to:

rac-cis 5-chloro-2-{4-[2-(2-{[5-(methylsulfonyl)pyridin-2-yl]oxy}ethyl)cyclopropyl]piperidin-1-yl}pyrimidine;
5-chloro-2-{4-[(1R,2S)-2-(2-{[5-(methylsulfonyl)pyridin-2-yl]oxy}ethyl)cyclopropyl]piperidin-1-yl}pyrimidine;
rac cis-5-chloro-2-[4-(2-{2-[4-(methylsulfonyl)phenoxy]ethyl}cyclopropyl)piperidin-1-yl]pyrimidine;
5-chloro-2-[4-((1S,2R)-2-{2-[4-(methylsulfonyl)phenoxy]ethyl}cyclopropyl) piperidin-1-yl]pyrimidine;
5-chloro-2-[4-((1R,2S)-2-{2-[4-(methylsulfonyl)phenoxy]ethyl}cyclopropyl) piperidin-1-yl]pyrimidine;
rac cis-5-chloro-2-[4-(2-{2-[3-(methylsulfonyl)phenoxy]ethyl}cyclopropyl)piperidin-1-yl]pyrimidine; and
rac cis-5-chloro-2-[4-(2-{2-[3-(5-methyl-1,3,4-oxadiazol-2-yl)phenoxy]ethyl}cyclopropyl) piperidin-1-yl]pyrimidine; and
pharmaceutically acceptable salts thereof.

Selective PPARγ modulators (SPPARγM's) that can be used in combination with the compounds of Formula I include, but are not limited to:

(2S)-2-({6-chloro-3-[6-(4-chlorophenoxy)-2-propylpyridin-3-yl]-1,2-benzisoxazol-5-yl}oxy)propanoic acid;
(2S)-2-({6-chloro-3-[6-(4-fluorophenoxy)-2-propylpyridin-3-yl]-1,2-benzisoxazol-5-yl}oxy)propanoic acid;
(2S)-2-{[6-chloro-3-(6-phenoxy-2-propylpyridin-3-yl)-1,2-benzisoxazol-5-yl]oxy}propanoic acid;
(2R)-2-({6-chloro-3-[6-(4-chlorophenoxy)-2-propylpyridin-3-yl]-1,2-benzisoxazol-5-yl}oxy)propanoic acid;
(2R)-2-{3-[3-(4-methoxy)benzoyl-2-methyl-6-(trifluoromethoxy)-1H-indol-1-yl]phenoxy}butanoic acid;
(2S)-2-{3-[3-(4-methoxy)benzoyl-2-methyl-6-(trifluoromethoxy)-1H-indol-1-yl]phenoxy}butanoic acid;
2-{3-[3-(4-methoxy)benzoyl-2-methyl-6-(trifluoromethoxy)-1H-indol-1-yl]phenoxy}-2-methylpropanoic acid; and
(2R)-2-{3-[3-(4-chloro)benzoyl-2-methyl-6-(trifluoromethoxy)-1H-indol-1-yl]phenoxy}propanoic acid; and
pharmaceutically acceptable salts thereof.

Inhibitors of 11β-hydroxysteroid dehydrogenase type 1 that can be used in combination with the compounds of Formula I include, but are not limited to:

3-[1-(4-chlorophenyl)-trans-3-fluorocyclobutyl]-4,5-dicyclopropyl-r-4H-1,2,4-triazole;
3-[1-(4-chlorophenyl)-trans-3-fluorocyclobutyl]-4-cyclopropyl-5-(1-methylcyclopropyl)-r-4H-1,2,4-triazole;
3-[1-(4-chlorophenyl)-trans-3-fluorocyclobutyl]-4-methyl-5-[2-(trifluoromethoxy)phenyl]-r-4H-1,2,4-triazole;
3-[1-(4-chlorophenyl)cyclobutyl]-4-methyl-5-[2-(trifluoromethyl)phenyl]-4H-1,2,4-triazole;
3-{4-[3-(ethylsulfonyl)propyl]bicyclo[2.2.2]oct-1-yl}-4-methyl-5-[2-(trifluoromethyl)phenyl]-4H-1,2,4-triazole;
4-methyl-3-{4-[4-(methylsulfonyl)phenyl]bicyclo[2.2.2]oct-1-yl}-5-[2-(trifluoromethyl)phenyl]-4H-1,2,4-triazole;
3-(4-{4-methyl-5-[2-(trifluoromethyl)phenyl]-4H-1,2,4-triazol-3-yl}bicyclo[2.2.2]oct-1-yl)-5-(3,3,3-trifluoropropyl)-1,2,4-oxadiazole;
3-(4-{4-methyl-5-[2-(trifluoromethyl)phenyl]-4H-1,2,4-triazol-3-yl}bicyclo[2.2.2]oct-1-yl)-5-(3,3,3-trifluoroethyl)-1,2,4-oxadiazole;
5-(3,3-difluorocyclobutyl)-3-(4-{4-methyl-5-[2-(trifluoromethyl)phenyl]-4H-1,2,4-triazol-3-yl}bicyclo[2.2.2]oct-1-yl)-1,2,4-oxadiazole;
5-(1-fluoro-1-methylethyl)-3-(4-{4-methyl-5-[2-(trifluoromethyl)phenyl]-4H-1,2,4-triazol-3-yl}bicyclo[2.2.2]oct-1-yl)-1,2,4-oxadiazole;
2-(1,1-difluoroethyl)-5-(4-{4-methyl-5-[2-(trifluoromethyl)phenyl]-4H-1,2,4-triazol-3-yl}bicyclo[2.2.2]oct-1-yl)-1,3,4-oxadiazole;
2-(3,3-difluorocyclobutyl)-5-(4-{4-methyl-5-[2-(trifluoromethyl)phenyl]-4H-1,2,4-triazol-3-yl}bicyclo[2.2.2]oct-1-yl)-1,3,4-oxadiazole; and
5-(1,1-difluoroethyl)-3-(4-{4-methyl-5-[2-(trifluoromethyl)phenyl]-4H-1,2,4-triazol-3-yl}bicyclo[2.2.2]oct-1-yl)-1,2,4-oxadiazole; and
pharmaceutically acceptable salts thereof.

AMP-activated Protein Kinase (AMPK) activators that can be used in combination with the compounds of Formula I include, but are not limited to:

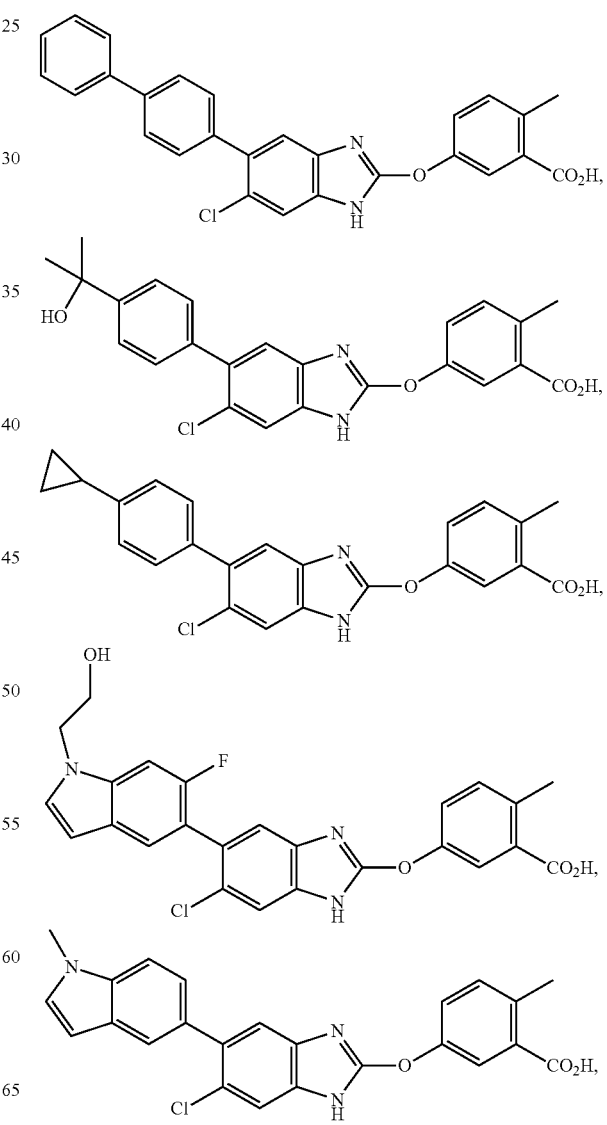

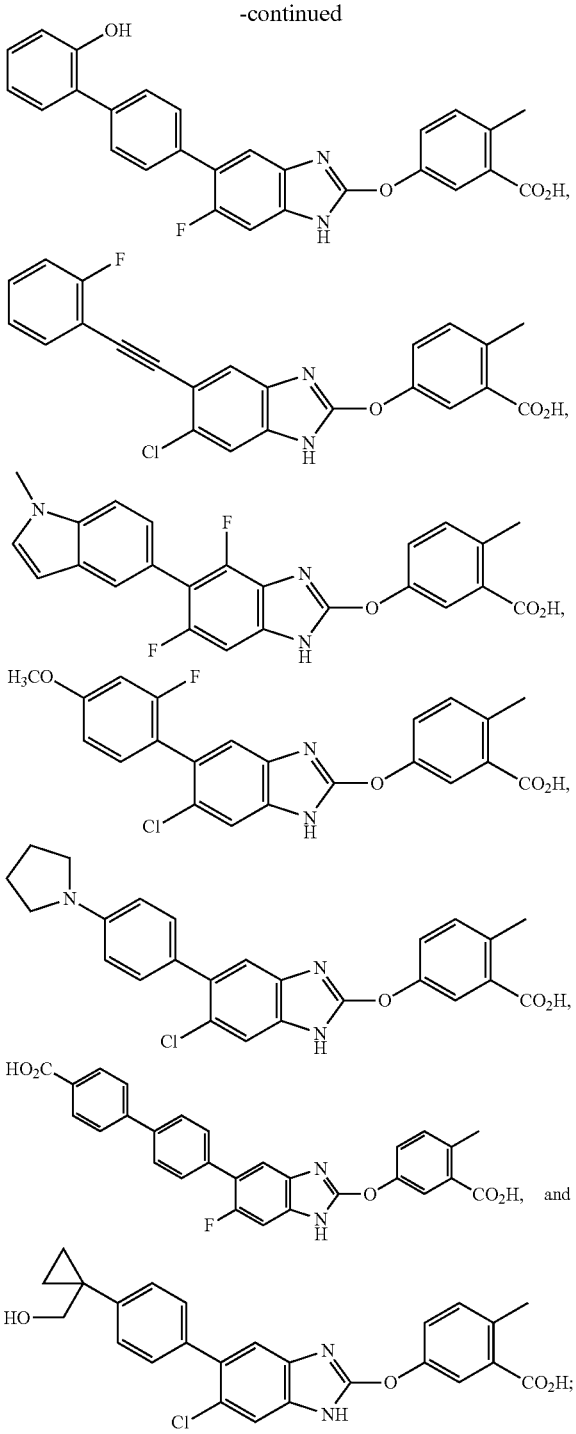

and pharmaceutically acceptable salts thereof.

Inhibitors of acetyl-CoA carboxylase-1 and 2 (ACC-1 and ACC-2) that can be used in combination with the compounds of Formula I include, but are not limited to:

3-{1'-[(1-cyclopropyl-4-methoxy-1H-indol-6-yl)carbonyl]-4-oxospiro[chroman-2,4'-piperidin]-6-yl}benzoic acid;

5-{1'-[(1-cyclopropyl-4-methoxy-1H-indol-6-yl)carbonyl]-4-oxospiro[chroman-2,4'-piperidin]-6-yl}nicotinic acid;

1'-[(1-cyclopropyl-4-methoxy-1H-indol-6-yl)carbonyl]-6-(11'-tetrazol-5-yl)spiro[chroman-2,4'-piperidin]-4-one;

1'-[(1-cyclopropyl-4-ethoxy-3-methyl-1H-indol-6-yl)carbonyl]-6-(1H-tetrazol-5-yl)spiro[chroman-2,4'-piperidin]-4-one;

5-{1'-[(1-cyclopropyl-4-methoxy-3-methyl-1H-indol-6-yl)carbonyl]-4-oxo-spiro[chroman-2,4'-piperidin]-6-yl}nicotinic acid;

4'-({6-(5-carbamoylpyridin-2-yl)-4-oxospiro[chroman-2,4'-piperidin]-1'-yl}carbonyl)-2',6'-diethoxybiphenyl-4-carboxylic acid;

2',6'-diethoxy-4'-{[6-(1-methyl-1H-pyrazol-4-yl)-4-oxospiro[chroman-2,4'-piperidin]-1'-yl]carbonyl}biphenyl-4-carboxylic acid;

2',6'-diethoxy-3-fluoro-4'-{[6-(1-methyl-1H-pyrazol-4-yl)-4-oxospiro[chroman-2,4'-piperidin]-1'-yl]carbonyl}biphenyl-4-carboxylic acid;

5-[4-({6-(3-carbamoylphenyl)-4-oxospiro[chroman-2,4'-piperidin]-1'-yl}carbonyl)-2,6-diethoxyphenyl]nicotinic acid;

sodium 4'-({6-(5-carbamoylpyridin-2-yl)-4-oxospiro[chroman-2,4'-piperidin]-1'-yl}carbonyl)-2',6'-diethoxybiphenyl-4-carboxylate;

methyl 4'-({6-(5-carbamoylpyridin-2-yl)-4-oxospiro[chroman-2,4'-piperidin]-1'-yl}carbonyl)-2',6'-diethoxybiphenyl-4-carboxylate;

1'-[(4,8-dimethoxyquinolin-2-yl)carbonyl]-6-(1H-tetrazol-5-yl)spiro[chroman-2,4'-piperidin]-4-one;

(5-{1'-[(4,8-dimethoxyquinolin-2-yl)carbonyl]-4-oxospiro[chroman-2,4'-piperidin]-6-yl}-2H-tetrazol-2-yl)methyl pivalate;

5-{1'-[(8-cyclopropyl-4-methoxyquinolin-2-yl)carbonyl]-4-oxospiro[chroman-2,4'-piperidin]-6-yl}nicotinic acid;

1'-(8-methoxy-4-morpholin-4-yl-2-naphthoyl)-6-(1H-tetrazol-5-yl)spiro[chroman-2,4'-piperidin]-4-one; and 1'-[(4-ethoxy-8-ethylquinolin-2-yl)carbonyl]-6-(1H-tetrazol-5-yl)spiro[chroman-2,4'-piperidin]-4-one; and pharmaceutically acceptable salts and esters thereof.

Methods of Administration

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals such as mice, rats, horses, cattle, sheep, dogs, cats, monkeys, etc., the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active object compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl or n-propyl p-hydroxybenzoate, one or more coloring agents, one or more flavoring agents, and one or more sweetening agents, such as sucrose or saccharin.

Oily suspensions may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions, etc., containing the compounds of the present invention are employed. (For purposes of this application, topical application shall include mouthwashes and gargles.)

The pharmaceutical composition and method of the present invention may further comprise other therapeutically active compounds as noted herein which are usually applied in the treatment of the above mentioned pathological conditions.

In the treatment or prevention of conditions which require inhibition of dipeptidyl peptidase-IV enzyme activity an appropriate dosage level will generally be about 0.01 to 500 mg per kg patient body weight per day which can be administered in single or multiple doses. Preferably, the dosage level will be about 0.1 to about 250 mg/kg per day; more preferably about 0.5 to about 100 mg/kg per day. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions are preferably provided in the form of tablets containing 1.0 to 1000 mg of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 mg of the active ingredient for the symptomatic adjustment of the dosage to the patient to be treated. The compounds may be administered on a regimen of 1 to 4 times per day, preferably once or twice per day.

When treating or preventing diabetes mellitus and/or hyperglycemia or hypertriglyceridemia or other diseases for which compounds of the present invention are indicated, generally satisfactory results are obtained when the compounds of the present invention are administered at a daily dosage of from about 0.1 mg to about 100 mg per kilogram of animal body weight, preferably given as a single daily dose or in divided doses two to six times a day, or in sustained release form. For most large mammals, the total daily dosage is from about 1.0 mg to about 1000 mg, preferably from about 1 mg to about 50 mg. In the case of a 70 kg adult human, the total daily dose will generally be from about 7 mg to about 350 mg. This dosage regimen may be adjusted to provide the optimal therapeutic response.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Synthetic methods for preparing the compounds of the present invention are illustrated in the following Schemes and Examples. Starting materials are commercially available or may be made according to procedures know in the art or as illustrated herein.

The intermediates and compounds of structural Formula I of the present invention can be prepared according to the procedures of the following Schemes and Examples using appropriate materials and are further exemplified by the following specific examples. These specific examples are provided so that the invention might be more fully understood and are to be considered illustrative only and should not be construed as limiting the invention in any way. The Examples further illustrate details for the preparation of the compounds of the present invention. Those skilled in the art will readily understand that known variations of the conditions and processes of the following preparative procedures can be used to prepare these compounds. All temperatures are degrees Celsius unless otherwise noted. Mass spectra (MS) were measured by electron-spray ion-mass spectroscopy. Proton NMR (H-NMR) spectra were measured at 500 MHz, and chemical shifts are provided as parts-per-million (ppm).

EXAMPLES

Compounds of the invention can be made using procedures known in the art. The following reaction schemes show exemplary procedures, but those skilled in the art will recognize that other procedures can also be suitable. Those skilled in the art will recognize that changes to the requisite reagents can be made at the appropriate Steps in the Methods outlined below. Reactions may involve monitoring for consumption of starting material, and there are many methods for said monitoring, including but not limited to thin layer chromatography (TLC) and liquid chromatography mass spectrometry (LCMS), and those skilled in the art will recognize that where one method is specified, other non-limiting methods may be substituted. Mass spectra (MS) were measured by electron-spray ion-mass spectroscopy. Proton NMR (HNMR) spectra were measured at 400 or 500 MHz, as indicated, and chemical shifts are provided as parts-per-million (ppm). Techniques, solvents and reagents may be referred to by their abbreviations as follows:

Benzyl: Bn
1,2-dimethoxyethane: DME
3-Chloroperoxybenzoic acid: mCPBA
Acetonitrile: MeCN
Dichloromethane: DCM
Diisopropylamine: iPr$_2$NH
Diisopropylethylamine: DIEA or iPr$_2$NEt
Dimethylacetamide: DMA
Dimethylformamide: DMF
Dimethylsulfoxide: DMSO
Ether or diethyl ether: Et$_2$O
Ethyl acetate: AcOEt or EtOAc
Grams: g
High performance liquid chromatography: HPLC
High resolution mass spectrometry: HRMS
Liquid chromatography mass Spectrometry: LCMS
Methanol: MeOH
Methyl magnesium bromide: MeMgBr
Microliters: μl
Milligrams: mg
Milliliters: mL
Millimoles: mmol
N-bromosuccinimide: NBS
n-Butyllithium: nBuLi
Nuclear magnetic resonance spectroscopy: NMR
paramethoxy benzyl: PMB
Retention time: t$_R$
Room temperature (ambient, ~25° C.): rt
tert-Butoxycarbonyl: t-Boc or Boc
Tetrahydrofuran: THF
Thin layer chromatography: TLC
Triethylamine: Et$_3$N or TEA
Trifluoroacetic acid: TFA Method 1

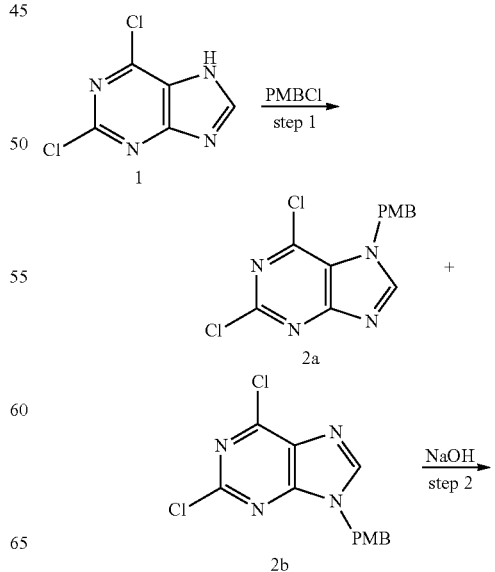

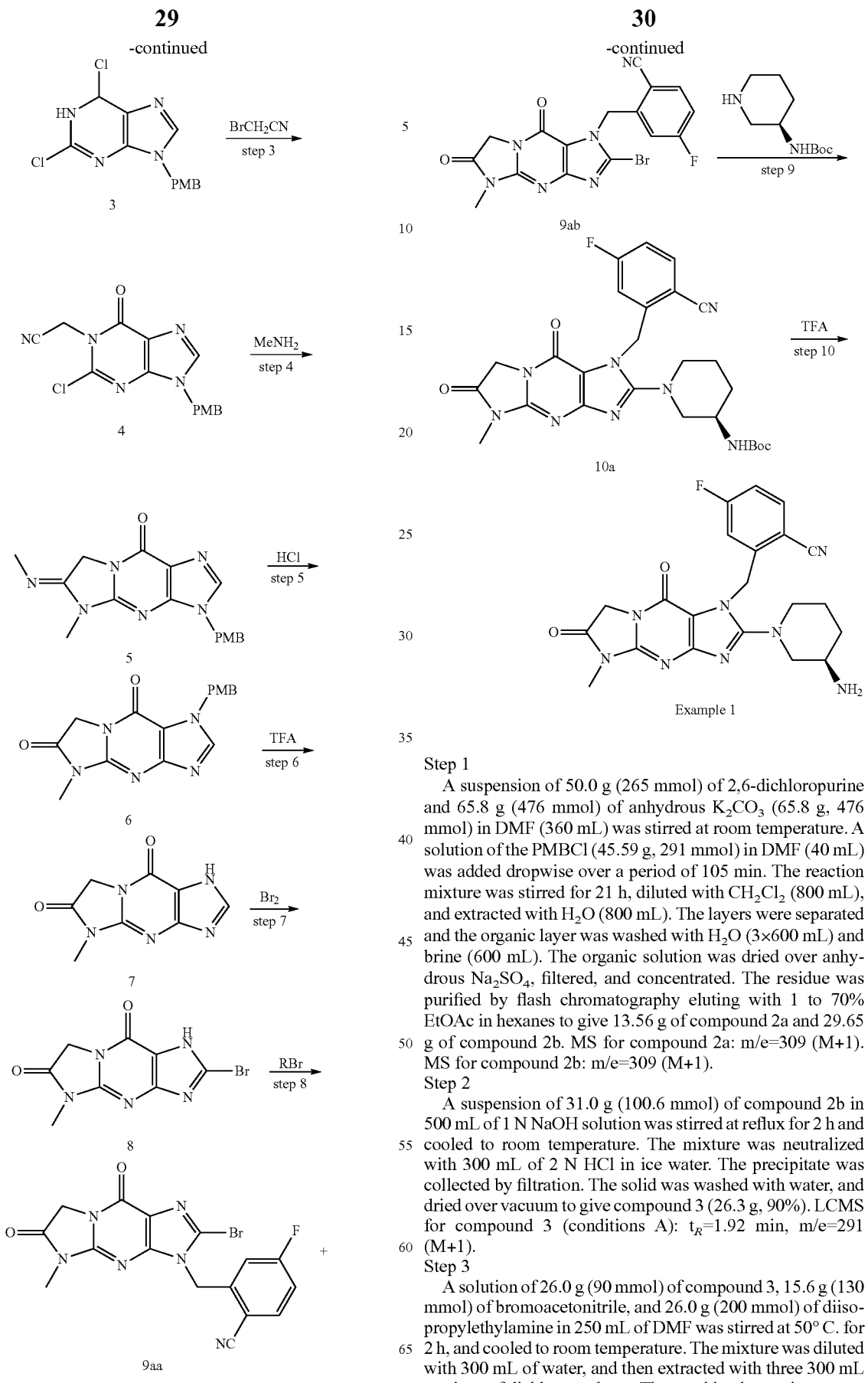

Step 1
A suspension of 50.0 g (265 mmol) of 2,6-dichloropurine and 65.8 g (476 mmol) of anhydrous $K_2CO_3$ (65.8 g, 476 mmol) in DMF (360 mL) was stirred at room temperature. A solution of the PMBCl (45.59 g, 291 mmol) in DMF (40 mL) was added dropwise over a period of 105 min. The reaction mixture was stirred for 21 h, diluted with $CH_2Cl_2$ (800 mL), and extracted with $H_2O$ (800 mL). The layers were separated and the organic layer was washed with $H_2O$ (3×600 mL) and brine (600 mL). The organic solution was dried over anhydrous $Na_2SO_4$, filtered, and concentrated. The residue was purified by flash chromatography eluting with 1 to 70% EtOAc in hexanes to give 13.56 g of compound 2a and 29.65 g of compound 2b. MS for compound 2a: m/e=309 (M+1). MS for compound 2b: m/e=309 (M+1).

Step 2
A suspension of 31.0 g (100.6 mmol) of compound 2b in 500 mL of 1 N NaOH solution was stirred at reflux for 2 h and cooled to room temperature. The mixture was neutralized with 300 mL of 2 N HCl in ice water. The precipitate was collected by filtration. The solid was washed with water, and dried over vacuum to give compound 3 (26.3 g, 90%). LCMS for compound 3 (conditions A): $t_R$=1.92 min, m/e=291 (M+1).

Step 3
A solution of 26.0 g (90 mmol) of compound 3, 15.6 g (130 mmol) of bromoacetonitrile, and 26.0 g (200 mmol) of diisopropylethylamine in 250 mL of DMF was stirred at 50° C. for 2 h, and cooled to room temperature. The mixture was diluted with 300 mL of water, and then extracted with three 300 mL portions of dichloromethane. The combined organic extracts were washed with 100 mL of brine, and concentrated. The residue was purified by flash chromatography eluting with a gradient of 5-95% ethyl acetate in hexanes to give compound 4 (16.2 g, 55%). LCMS for 4 (conditions B): $t_R$=1.71 min, m/e=330 (M+1).

Step 4

A suspension of 6.6 g (20 mmol) of compound 4 and 4.0 g (52 mmol) of 40% MeNH$_2$ in water was stirred at room temperature for 18 h. The mixture was concentrated to give crude compound 5, which was used in the next step without purification. LCMS for 5 (conditions A): $t_R$=1.73 min, m/e=339 (M+1).

Step 5

A solution of compound 5 mentioned above and 20 mL of 6 N HCl in 80 mL of MeOH was stirred at reflux for 3 h. It was concentrated; the residue was neutralized with 200 mL of saturated NaHCO$_3$ solution. The mixture was extracted with four 200 mL portions of dichloromethane. The combined organic extracts were concentrated to give compound 6 (6.6 g, 100%). LCMS for 6 (conditions A): $t_R$=1.93 min, m/e=326 (M+1).

Step 6

A suspension of 0.85 g (2.62 mmol) of compound 6 in 15 mL of TFA in a sealed tube was heated at 100° C. in microwave for 5 h. It was concentrated; the residue was triturated with ether and small amount of MeOH, and filtered to give compound 7 (0.50 g, 93%) as a TFA salt. LCMS for 7 (conditions A): $t_R$=0.87 min, m/e=206 (M+1).

Step 7

To a suspension of 0.50 g (2.44 mmol) of compound 7 in 70 mL of MeCN was added 1.0 g (excess) of bromine dropwise. The mixture was stirred at room temperature for 20 h, and concentrated to give crude compound 8 (0.78 g) as a TFA salt. LCMS for 8 (conditions B): $t_R$=0.60 min, m/e=284 (M+1).

Step 8

A solution of 2.5 g (6.85 mmol) of compound 8 (TFA salt), 1.91 g (8.9 mmol) of 2-cyano-5-fluorobenzyl bromide, and 1.77 g (13.7 mmol) of diisopropylethylamine in 15 mL of DMF was stirred at room temperature for 3 h, and concentrated. The residue was purified by flash chromatography eluting with 0-3% MeOH in CH$_2$Cl$_2$ plus 1% NH$_4$OH to give compound 9aa (0.615 g) and 9ab (0.676 g). LCMS for 9aa (conditions A): $t_R$=2.04 min, m/e=417 (M+1). LCMS for 9ab (conditions A): $t_R$=2.02 min, m/e=417 (M+1).

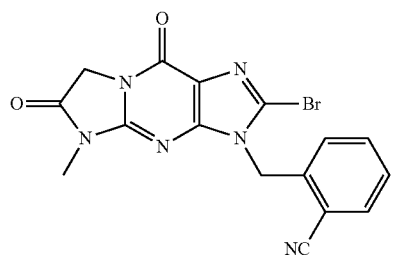
9ba

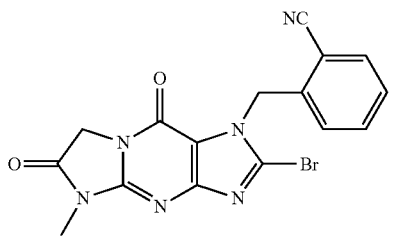
9bb

Compounds 9ba and 9bb were prepared analogously. LCMS for 9ba (conditions B): $t_R$=1.54 min, m/e=399 (M+1). LCMS for 9bb (conditions B): $t_R$=1.52 min, m/e=399 (M+1).

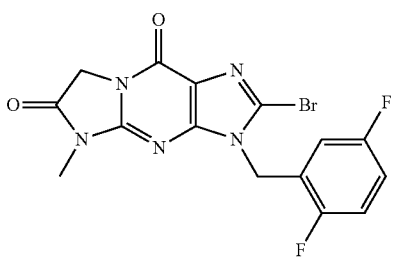
9ca

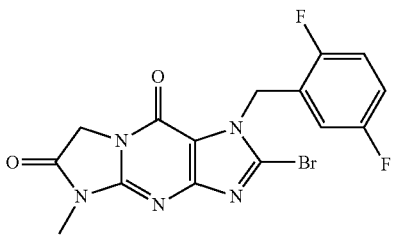
9cb

Compounds 9ca and 9cb were prepared analogously. LCMS for 9ca (conditions A): $t_R$=2.13 min, m/e=410 (M+1). LCMS for 9cb (conditions A): $t_R$=2.11 min, m/e=410 (M+1).

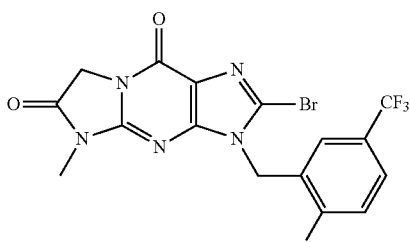
9da

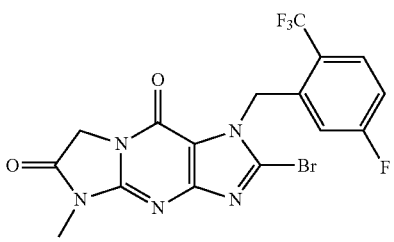
9db

Compounds 9da and 9db were prepared analogously.
LCMS for 9da (conditions A): $t_R$=2.24 min, m/e=460 (M+1).
LCMS for 9db (conditions A): $t_R$=2.22 min, m/e=460 (M+1).

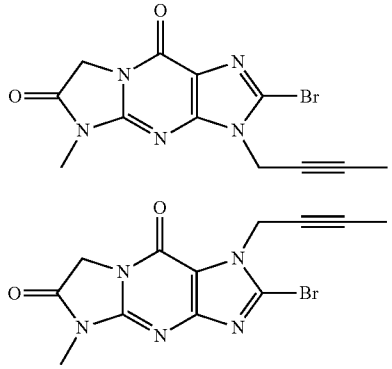

9ea

9eb

Compounds 9ea and 9eb were prepared analogously.
LCMS for 9ea (conditions B): $t_R$=1.46 min, m/e=336 (M+1).
LCMS for 9eb (conditions B): $t_R$=1.42 min, m/e=336 (M+1).

Step 9

A solution of 0.60 g (1.44 mmol) of compound 9ab, 0.288 g (1.44 mmol) of (R)-3-(Boc-amino) piperidine, and 0.24 g (1.87 mmol) of diisopropylethylamine in 15 mL of MeCN was stirred at 90° C. for 18 h, and concentrated. The residue was purified by flash chromatography eluting with 0-5% MeOH in $CH_2Cl_2$ plus 1% $NH_4OH$ to give a crude product, which was further purified by preparative TLC eluting with 7% MeOH in $CH_2Cl_2$ to give pure compound 10a (0.226 g, 29%). LCMS for 10a (conditions A): $t_R$=2.22 min, m/e=537 (M+1).

Compounds 10b-10e were prepared analogously.

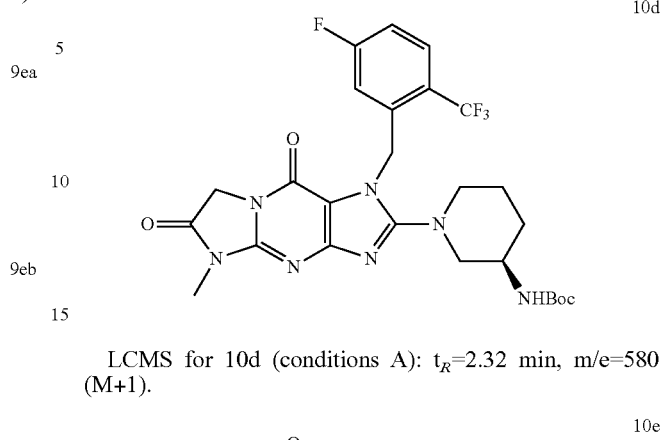

10b

LCMS for 10b (conditions B): $t_R$=1.77 min, m/e=519 (M+1).

10c

LCMS for 10c (conditions A): $t_R$=2.24 min, m/e=530 (M+1).

10d

LCMS for 10d (conditions A): $t_R$=2.32 min, m/e=580 (M+1).

10e

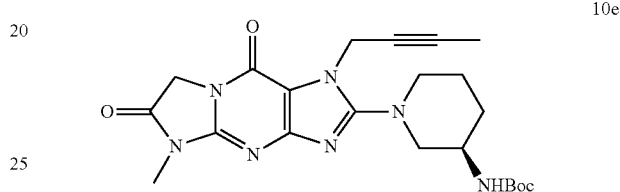

LCMS for 10e (conditions B): $t_R$=1.71 min, m/e=456 (M+1).

Step 10

A solution of 0.22 g (0.41 mmol) of compound 10a and 2.0 g of TFA in 2 mL of $CH_2Cl_2$ was stirred at room temperature for 20 h, and concentrated. The residue was purified by flash chromatography eluting with 0-7% MeOH in $CH_2Cl_2$ plus 1% $NH_4OH$ to give example 1, which was treated with HCl in ether to form HCl salt (0.184 g, 95%). LCMS for example 1 (conditions A): $t_R$=2.18 min, m/e=437 (M+1).

Examples 2-5 were prepared analogously.

Example 2

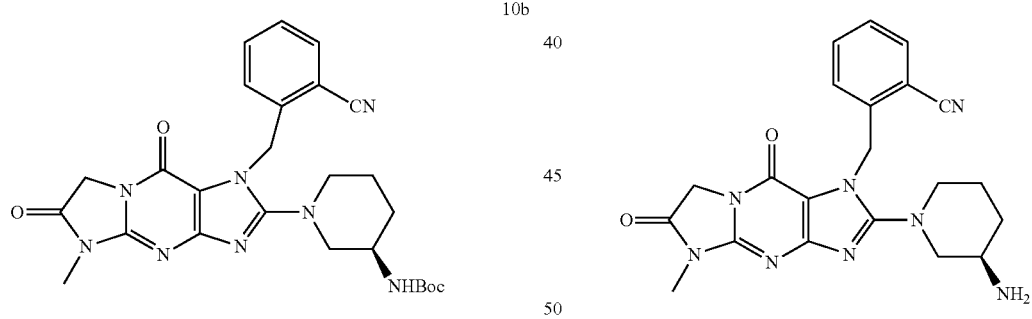

LCMS for example 2 (conditions B): $t_R$=1.25 min, m/e=419 (M+1).

Example 3

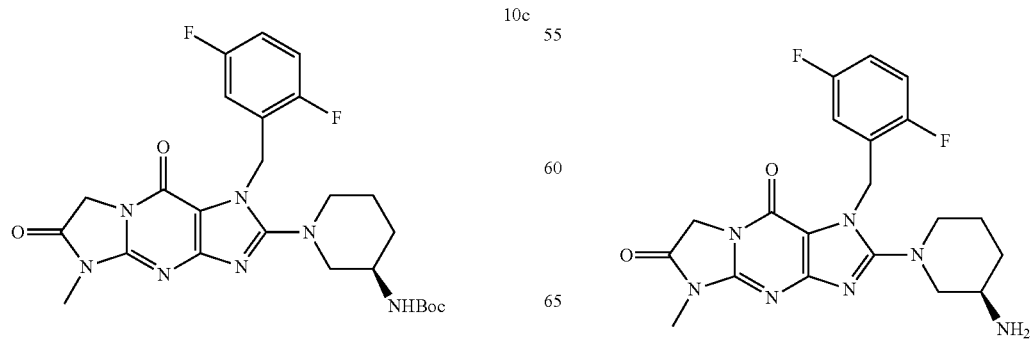

LCMS for example 3 (conditions A): $t_R$=1.88 min, m/e=437 (M+1).
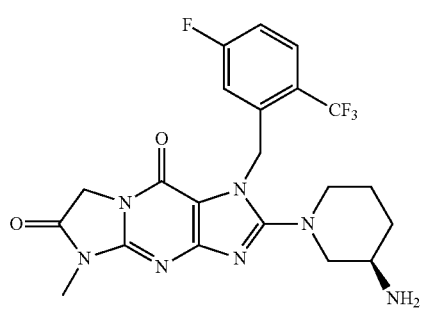
LCMS for example 4 (conditions A): $t_R$=1.93 min, m/e=480 (M+1).
Example 5
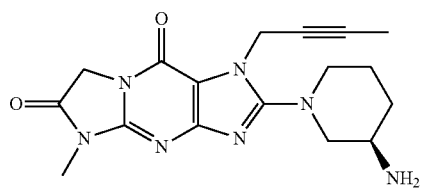
LCMS for example 5 (conditions B): $t_R$=1.12 min, m/e=356 (M+1).
Method 2
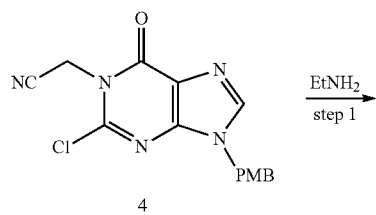
4
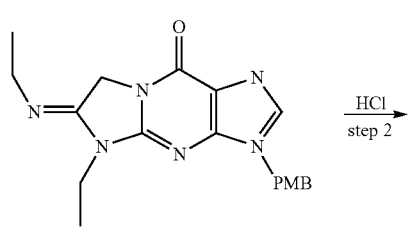
11a
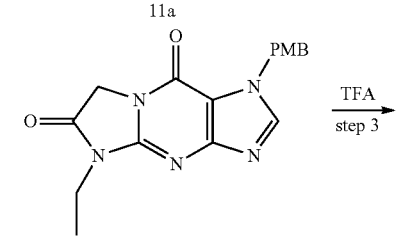
12
-continued
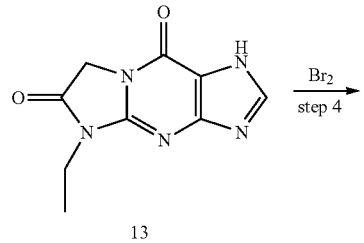
13
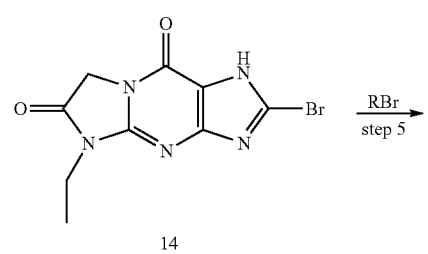
14
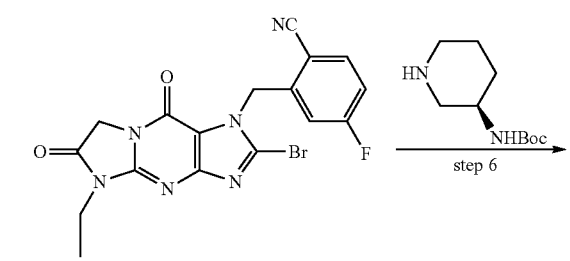
15aa
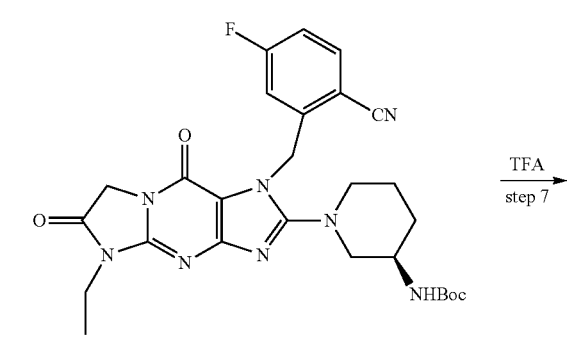
15ab
16a

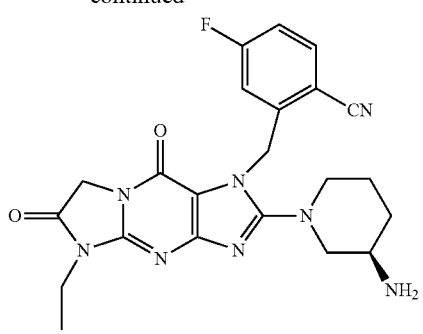

Example 6

Step 1

Using the procedure described in step 4 of Method 1, compound 4 was converted to compound 11a. Compound 11a was used directly in step 2.

Compounds 11b, 11c, and 11d were prepared analogously from treatment of compound 4 with various amines.

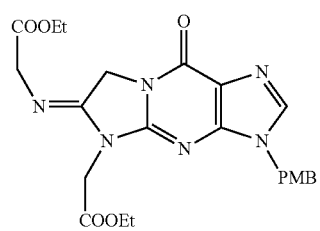

11b

LCMS for 11b (conditions A): $t_R$=1.67 min, m/e=399 (M+1).

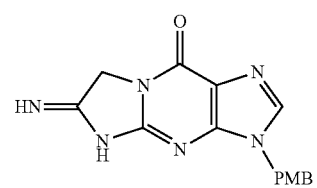

11c

LCMS for 11c (conditions B): $t_R$=1.76 min, m/e=483 (M+1).

11d

LCMS for 11d (conditions B): $t_R$=1.23 min, m/e=311 (M+1).

Step 2

Using the procedure described in step 5 of Method 1, compound 11a was converted to compound 12. HNMR (400 MHz, CDCl$_3$) δ 7.6 (s, 1 H), 7.22 (d, J=8.6 Hz, 2 H), 6.86 (d, J=8.6 Hz, 2 H), 5.19 (s, 2 H), 4.54 (s, 2 H), 3.87 (q, J=7.0 Hz, 2 H), 3.78 (s, 3 H), 1.35 (t, J=7.0 Hz, 3 H).

Step 3

Using the procedure described in step 6 of Method 1, compound 12 was converted to compound 13. HNMR (400 MHz, d$_6$-DMSO) δ 8.19 (s, 1 H), 4.49 (s, 2 H), 3.66 (q, J=7.0 Hz, 2 H), 1.19 (t, J=7.0 Hz, 3 H).

Step 4

Using the procedure described in step 6 of Method 1, compound 13 was converted to compound 14. H NMR (400 MHz, d$_6$-DMSO) δ 4.37 (s, 2 H), 3.60 (q, J=6.8 Hz, 2 H), 1.35 (t, J=6.8 Hz, 3 H). LCMS for 14 (conditions A): $t_R$=1.22 min, m/e=298 (M+1).

Step 5

Using the procedure described in step 6 of Method 1, compound 14 was converted to compounds 15aa and 15ab. MS for 15aa (ESI-MS): m/e=433 (M+1). MS for 15ab (ESI-MS): m/e=433 (M+1).

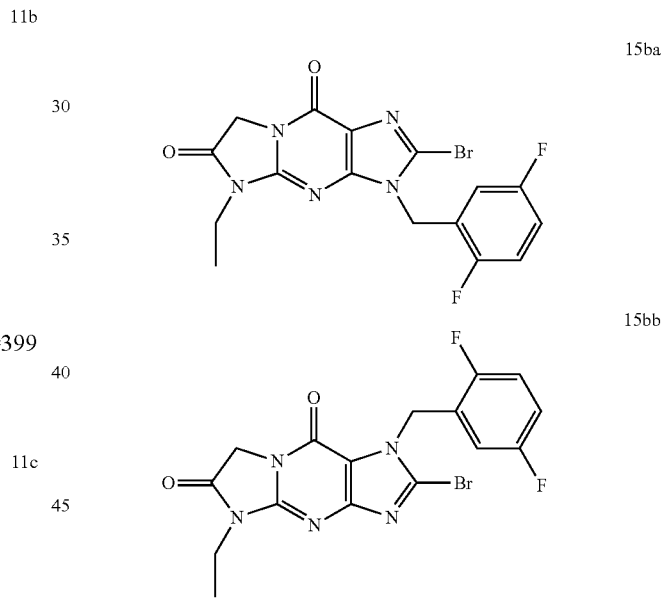

Compounds 15ba and 15bb were prepared analogously. LCMS for 15ba (conditions A): $t_R$=2.20 min, m/e=424 (M+1). LCMS for 15bb (conditions A): $t_R$=2.19 min, m/e=424 (M+1).

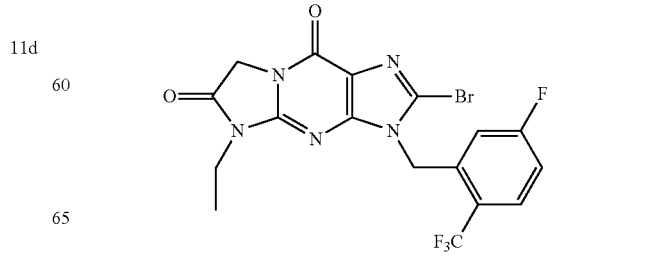

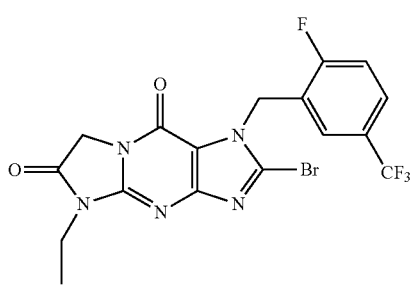

15cb

Compounds 15ca and 15cb were prepared analogously. LCMS for 15ca (condition A): $t_R$=2.29 min, m/e=476 (M+1). LCMS for 15cb (condition A): $t_R$=2.28 min, m/e=476 (M+1).
Step 6 and Step 7

Using the procedures described in step 6 and step 7 of Method 1, compound 15ab was converted to example 6. LCMS for example 6 (condition A): $t_R$=1.86 min, m/e=451 (M+1).

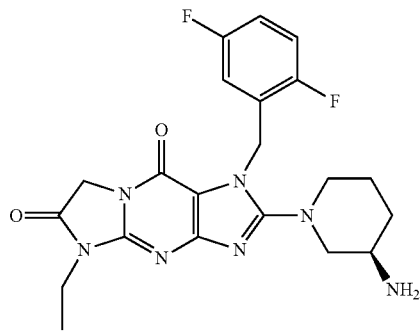

Example 7

Example 7 was prepared from 15bb analogously. LCMS for example 7 (condition A): $t_R$=1.90 min, m/e=444 (M+1).

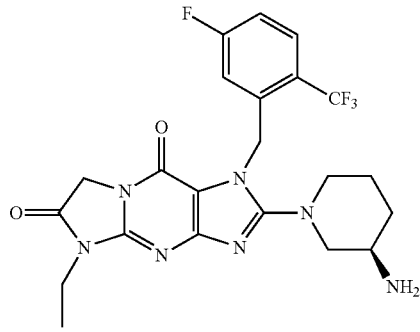

Example 8

Example 8 was prepared from 15cb analogously. LCMS for example 8 (condition A): $t_R$=1.94 min, m/e=494 (M+1).

LC/MS Conditions
Conditions A:
Column: Agilent SBC18 (3.0×50 mm) 1.8 uM
  Mobile phase: A: 0.1% Trifluoroacetic acid in water
    B: 0.1% Trifluoroacetic acid in acetonitrile
Gradient: 90:10 (A:B) for 0.3 min, 90:10 to 5:95 (A:B) over 1.2 min, 5:95 (A:B) for 1.2 min.
Flow rate: 1.0 mL/min
  UV detection: 254 and 220 nm
  Mass spectrometer: Agilent 6140 quadrupole.
Conditions B:
Column: Agilent SBC18 (3.0×50 mm) 1.8 uM
  Mobile phase: A: 0.05% Trifluoroacetic acid/0.5% Acetic acid in water
    B: 0.05% Trifluoroacetic acid/0.1% Acetic acid in acetonitrile
Gradient: 90:10 (A:B) for 1.5 min, 90:10 to 5:95 (A:B) over 1.2 min, 5:95 to 90:10 (A:B) for 0.9 min.
Flow rate: 1.0 mL/min
  UV detection: 254 and 220 nm
  Mass spectrometer: Agilent 6140 quadrupole.
ESI-MS: Electro Spray Ionization Liquid chromatography-mass spectrometry (ESI-LC/MS) was performed on a PE SCIEX API-150EX, single quadrupole mass spectrometer.

Assay
DPP4 Enzyme Inhibition Assay (IC50 Measurement)
DPP4 activity was measured using a continuous fluorometric assay. The substrate, Gly-Pro-AMC, was cleaved by DPP4 to release the fluorescent AMC group. The reaction was monitored at the excitation wavelength of 360 nm and emission wavelength of 460 nm in a black 384-well plate using a PHERAstar Plus plate reader (BMG Labtech., Inc.) set at 37° C. The 30 μl assay solution contained 20 pM recombinant human DPP4 and 50 μM Gly-Pro-AMC substrate in assay buffer (100 mM HEPES, 100 mM NaCl, 0.1 mg/ml BSA, pH 7.5). The reaction was linear for at least 30 min (initial velocity) after addition of the substrate (no inhibitor control). All materials and reagents were pre-incubated at 37° C. prior to start of the experiment. Test compounds were serially diluted (3-fold) in 100% DMSO to avoid solubility issues; working solutions in 3% DMSO were prepared using assay buffer. 10 μl each of enzyme and compound solutions were mixed and pre-incubated at 37° C. for 30 minutes. 10 μl substrate (pre-incubated at 37° C.) was added and the plate was immediately loaded and shaken (5 sec.) prior to signal detection. The final concentration of DMSO was 1%. The initial velocity (slope of the reaction curve) was calculated using linear regression fit using the MARS software (BMG Labtech., Inc.). IC50 calculations are done by fitting the data to a non-linear (inhibitor) dose-response equation using Prism software.

| Biological data | |
|---|---|
| Example No. | DPP-IV IC$_{50}$ (nM) |
| Example 1 | 1.7 |
| Example 2 | 10.6 |
| Example 3 | 156 |
| Example 4 | 27.4 |
| Example 5 | 123 |
| Example 6 | 13.5 |
| Example 7 | 625 |
| Example 8 | 11.2 |

EXAMPLE OF A PHARMACEUTICAL FORMULATION

As a specific embodiment of an oral pharmaceutical composition, a 100 mg potency tablet is composed of 100 mg of any one of the Examples, 268 mg microcrystalline cellulose, 20 mg of croscarmellose sodium, and 4 mg of magnesium stearate. The active, microcrystalline cellulose, and croscarmellose are blended first. The mixture is then lubricated by magnesium stearate and pressed into tablets.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in responsiveness of the mammal being treated for any of the indications with the compounds of the invention indicated above. The specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed is:
1. A compound of structural formula I:

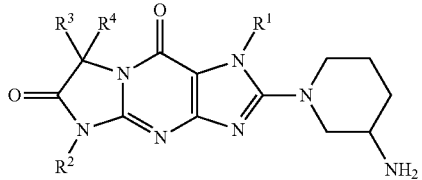

or a pharmaceutically acceptable salts thereof; wherein
$R^1$ is selected from the group consisting of $C_1$-$C_6$alkyl, $C_2$-$C_6$alkenyl, $C_2$-$C_6$alkynyl, $C_3$-$C_{10}$cycloalkyl, benzyl, heterocycle and $C_1$-$C_6$alkylheterocycle; wherein the $C_1$-$C_6$alkyl, $C_2$-$C_6$alkenyl, $C_2$-$C_6$alkynyl, $C_3$-$C_{10}$cycloalkyl, benzyl, heterocycle and $C_1$-$C_6$alkylheterocycle are unsubstituted or substituted with 1-3 substituents each independently selected from $R^5$;
$R^2$, $R^3$ and $R^4$ are independently selected from the group consisting of hydrogen and $C_1$-$C_6$ alkyl wherein the $C_1$-$C_6$ alkyl is unsubstituted or substituted with one or more substituents selected from $R^5$; and
$R^5$ is selected from the group consisting of hydrogen, halogen, $C_1$-$C_6$alkyl, halogen-substituted$C_1$-$C_6$alkyl, —OH, $C_1$-$C_6$alkylOH, halogen-substituted$C_1$-$C_6$alkylOH, —O$C_1$-$C_6$alkyl, —Ohalogen-substituted$C_1$-$C_6$alkyl, —COOH, —COO$C_1$-$C_6$alkyl, —$C_1$-$C_6$alkylCOO$C_1$-$C_6$alkyl, —$C_1$-$C_6$alkylCOOH, —O$C_1$-$C_6$alkylCOOH, —CN, $C_1$-$C_6$alkylCN, $NH_2$, NHC$_1$-$C_6$alkyl, N($C_1$-$C_6$alkyl)$_2$, —NHCOO$C_1$-$C_6$alkyl, $C_1$-$C_6$alkylCONH$_2$, —CONH$_2$, —CONHC$_1$-$C_6$alkyl, —NHCOC$_1$-$C_6$alkyl, —CON($C_1$-$C_6$alkyl)$_2$, —NHSO$_2$C$_1$-$C_6$alkyl, SO$_2$aryl, —SO$_2$C$_1$-$C_6$alkyl, $C_1$-$C_6$alkyl SO$_2$C$_1$-$C_6$alkyl, aryl, —NHCOaryl, and —NHCOheterocycle.

2. The compounds of claim 1 or pharmaceutically acceptable salts thereof wherein $R^1$ is substituted with 1 to 3 substituents selected from $R^5$.

3. The compounds of claim 1 or pharmaceutically acceptable salts thereof wherein $R^1$ is $C_1$-$C_6$alkyl.

4. The compounds of claim 1 or pharmaceutically acceptable salts thereof wherein $R^1$ is benzyl.

5. The compounds of claim 1 or pharmaceutically acceptable salts thereof wherein $R^2$ is unsubstituted.

6. The compounds of claim 1 or pharmaceutically acceptable salts thereof wherein $R^2$ is hydrogen.

7. The compounds of claim 1 or pharmaceutically acceptable salts thereof wherein $R^2$ is $C_1$-$C_6$alkyl.

8. The compounds of claim 1 any one of claims 1 or pharmaceutically acceptable salts thereof wherein $R^3$ is hydrogen.

9. The compounds of claim 1 or pharmaceutically acceptable salts thereof wherein $R^3$ is $C_1$-$C_6$alkyl.

10. The compounds of claim 1 or pharmaceutically acceptable salts thereof wherein $R^4$ is hydrogen.

11. The compounds of claim 1 or pharmaceutically acceptable salts thereof wherein $R^4$ is $C_1$-$C_6$alkyl.

12. The compounds of claim 1 or pharmaceutically acceptable salts thereof wherein $R^1$ is selected from the group consisting of methyl, benzyl, 2-fluorobenzyl, 2-butenyl, 2-butynyl, 2-propenyl, benzyl, 2,5-difluorobenzyl, 2,4,5-trifluorobenzyl, 2-cyanobenzyl, 2-cyano-5-fluorobenzyl, 2-cyano-4,5-difluorobenzyl, 2,4-dichlorobenzyl, and 2,5-dichlorobenzyl, wherein the methyl, 2-butenyl and benzyl are unsubstituted or substituted with 1-3 substituents selected from $R^5$.

13. The compounds of claim 1 or pharmaceutically acceptable salts thereof wherein $R^2$ is selected from the group consisting of 2-butynyl, 2-butenyl and benzyl, wherein the benzyl is unsubstituted or substituted with 1-3 substituents selected from the group $R^5$.

14. The compounds of claim 1 or pharmaceutically acceptable salts thereof wherein $R^5$ is selected from the group consisting of trifluoromenthyl, halogen and —CN.

15. A compound or pharmaceutically acceptable salt, selected from the group consisting of:

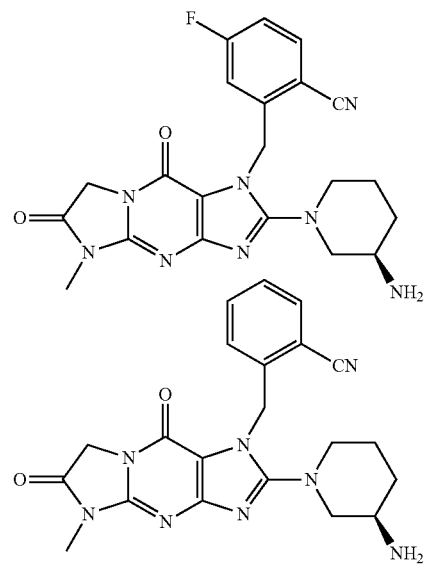

-continued

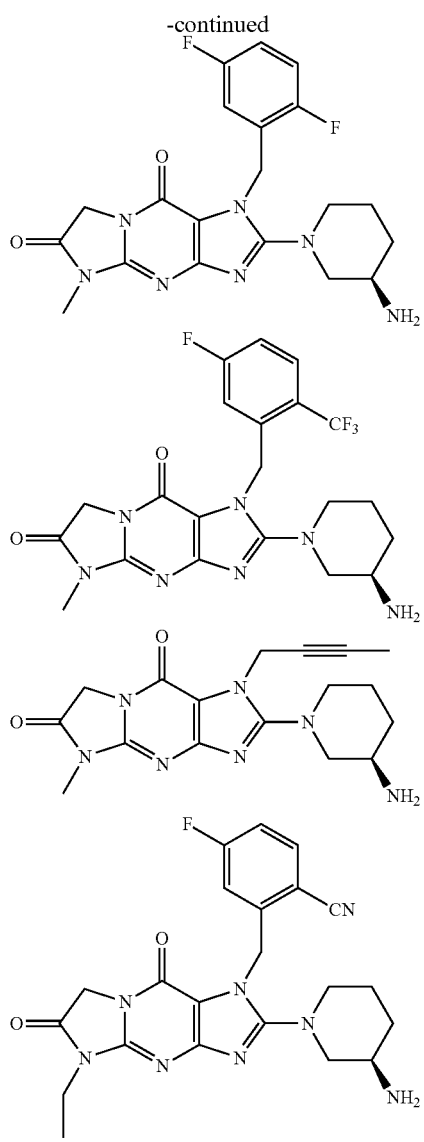

-continued

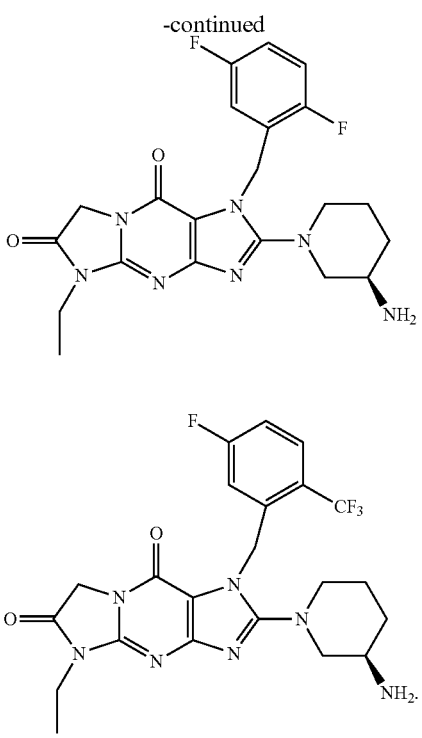

16. A pharmaceutical composition which comprises a compound of claim 1 and a pharmaceutically acceptable carrier.

17. The pharmaceutical composition of claim 16 additionally comprising a second agent selected from the group consisting of metformin, pioglitazone, rosiglitazone, a sulfonylurea, and an HMG-CoA reductase inhibitor.

18. A method of treating a condition selected from the group consisting of insulin resistance, hyperglycemia, and Type 2 diabetes by administering a therapeutically effective amount of a compounds of claim 1, or a pharmaceutically acceptable salt thereof to a patient in need thereof.

\* \* \* \* \*